(12) United States Patent
Militello et al.

(10) Patent No.: US 11,819,590 B2
(45) Date of Patent: Nov. 21, 2023

(54) APPARATUS AND METHODS FOR COATING MEDICAL DEVICES

(71) Applicant: Surmodics, Inc., Eden Prairie, MN (US)

(72) Inventors: Michael Militello, Eden Prairie, MN (US); Ralph A. Chappa, Ham Lake, MN (US); Alvin A. Kucera, Maple Grove, MN (US)

(73) Assignee: Surmodics, Inc., Eden Prairie, MN (US)

( * ) Notice: Subject to any disclaimer, the term of this patent is extended or adjusted under 35 U.S.C. 154(b) by 394 days.

(21) Appl. No.: 15/930,128

(22) Filed: May 12, 2020

(65) Prior Publication Data
US 2020/0360572 A1 Nov. 19, 2020

Related U.S. Application Data

(60) Provisional application No. 62/846,920, filed on May 13, 2019.

(51) Int. Cl.
*A61L 31/00* (2006.01)
*B05C 21/00* (2006.01)
*B05C 5/02* (2006.01)

(52) U.S. Cl.
CPC .......... *A61L 31/005* (2013.01); *B05C 5/0216* (2013.01); *B05C 21/00* (2013.01); *A61L 2420/02* (2013.01); *B05C 5/0241* (2013.01)

(58) Field of Classification Search
None
See application file for complete search history.

(56) References Cited

U.S. PATENT DOCUMENTS

| 273,410 A | 3/1883 | Wadleigh et al. |
| 554,114 A | 2/1896 | Evertz |
| 1,281,672 A | 10/1918 | Schorn |
| 1,866,100 A | 7/1932 | Hach |
| 2,253,019 A | 8/1941 | Crepeau |

(Continued)

FOREIGN PATENT DOCUMENTS

| CA | 2351016 | 12/2001 |
| DE | 3335502 | 3/1985 |

(Continued)

OTHER PUBLICATIONS

Braun, Dietrich "Plastics," Concise Encyclopedia of Polymer Science and Engineering, 1990 (pp. 461-464).

(Continued)

*Primary Examiner* — Jethro M. Pence
(74) *Attorney, Agent, or Firm* — Pauly, DeVries Smith & Deffner LLC

(57) ABSTRACT

Aspects herein relate to apparatus and methods for coating medical devices. In an embodiment, a coating system is included having a two-part fluid applicator defining a central channel, the two-part fluid applicator can include a first part having a first degree of flexibility; and a second part having a second degree of flexibility. The system can further include a fluid supply conduit in fluid communication with the fluid applicator; and a fluid supply reservoir in fluid communication with the fluid supply conduit. Other embodiments are also included herein.

20 Claims, 9 Drawing Sheets

(56) References Cited

U.S. PATENT DOCUMENTS

| | | | |
|---|---|---|---|
| 2,329,438 | A | 9/1943 | Fiedler |
| 2,330,880 | A | 10/1943 | Gladfelter et al. |
| 2,335,116 | A | 11/1943 | Hansen |
| 2,398,506 | A | 4/1946 | Rogers |
| 2,493,787 | A | 1/1950 | Torretti |
| 2,781,280 | A | 2/1957 | Miller |
| 2,821,158 | A | 1/1958 | Brown et al. |
| 2,881,461 | A | 4/1959 | Parker |
| 3,198,170 | A | 8/1965 | Toshio |
| 3,318,281 | A | 5/1967 | Plegat |
| 3,348,964 | A | 10/1967 | Good et al. |
| 3,416,530 | A | 12/1968 | Ness |
| 3,502,494 | A | 3/1970 | Ishiwata et al. |
| 3,625,214 | A | 12/1971 | Higuchi |
| 3,645,773 | A | 2/1972 | Herzhoff et al. |
| 3,663,292 | A | 5/1972 | Herzhoff et al. |
| 3,669,917 | A | 6/1972 | Ando et al. |
| 3,699,917 | A | 10/1972 | Deverse et al. |
| 3,702,739 | A | 11/1972 | Rentfrow |
| 3,723,120 | A | 3/1973 | Hummel et al. |
| 3,736,199 | A | 5/1973 | Mason |
| 3,837,805 | A | 9/1974 | Boucher |
| 3,935,896 | A | 2/1976 | Tegtmeier et al. |
| 3,936,549 | A | 2/1976 | Kohler et al. |
| 3,963,069 | A | 6/1976 | Marti et al. |
| 3,966,120 | A | 6/1976 | Furgalus et al. |
| 4,000,745 | A | 1/1977 | Goldberg |
| 4,016,306 | A | 4/1977 | Miyagawa et al. |
| 4,051,805 | A | 10/1977 | Waldrum |
| 4,060,116 | A | 11/1977 | Frailly |
| 4,069,307 | A | 1/1978 | Higuchi et al. |
| 4,073,335 | A | 2/1978 | Fort et al. |
| 4,075,975 | A | 2/1978 | Oswald |
| 4,082,870 | A | 4/1978 | Yenni |
| 4,144,317 | A | 3/1979 | Higuchi et al. |
| 4,146,036 | A | 3/1979 | Dutcher et al. |
| 4,148,934 | A | 4/1979 | Baker |
| 4,153,201 | A | 5/1979 | Berger et al. |
| 4,174,678 | A | 11/1979 | Van Den Bergh |
| 4,195,637 | A | 4/1980 | Gruntzig et al. |
| 4,196,231 | A | 4/1980 | Hubers |
| 4,197,338 | A | 4/1980 | Perna |
| 4,206,756 | A | 6/1980 | Grossan |
| 4,209,019 | A | 6/1980 | Dutcher et al. |
| 4,240,373 | A | 12/1980 | Anger |
| 4,257,343 | A | 3/1981 | Kullander |
| 4,289,089 | A | 9/1981 | Tacke et al. |
| 4,292,965 | A | 10/1981 | Nash |
| 4,300,557 | A | 11/1981 | Refojo et al. |
| 4,301,968 | A | 11/1981 | Berger et al. |
| 4,304,765 | A | 12/1981 | Shell et al. |
| 4,337,896 | A | 7/1982 | Berger et al. |
| 4,352,459 | A | 10/1982 | Berger et al. |
| 4,364,879 | A | 12/1982 | Gut et al. |
| 4,375,820 | A | 3/1983 | Vinarcsik et al. |
| 4,415,654 | A | 11/1983 | Pohl |
| 4,475,972 | A | 10/1984 | Wong |
| 4,503,802 | A | 3/1985 | Keller et al. |
| 4,541,564 | A | 9/1985 | Berger et al. |
| 4,544,626 | A | 10/1985 | Sullivan |
| 4,567,934 | A | 2/1986 | Nakao et al. |
| 4,572,451 | A | 2/1986 | Ikeda et al. |
| 4,575,330 | A | 3/1986 | Hull |
| 4,603,058 | A | 7/1986 | Adams |
| 4,616,593 | A | 10/1986 | Kawamura et al. |
| 4,622,917 | A | 11/1986 | Schramm |
| 4,638,045 | A | 1/1987 | Kohn et al. |
| 4,655,393 | A | 4/1987 | Berger |
| 4,678,466 | A | 7/1987 | Rosenwald |
| 4,723,708 | A | 2/1988 | Berger et al. |
| 4,743,252 | A | 5/1988 | Martin, Jr. et al. |
| 4,764,377 | A | 8/1988 | Goodson |
| 4,819,661 | A | 4/1989 | Heil et al. |
| 4,824,017 | A | 4/1989 | Mansfield |
| 4,853,224 | A | 8/1989 | Wong |
| 4,863,457 | A | 9/1989 | Lee et al. |
| 4,892,736 | A | 1/1990 | Goodson |
| 4,927,741 | A | 5/1990 | Garth et al. |
| 4,953,564 | A | 9/1990 | Berthelsen |
| 4,959,217 | A | 9/1990 | Sanders et al. |
| 4,971,895 | A | 11/1990 | Sullivan |
| 4,972,848 | A | 11/1990 | Di Domenico et al. |
| 4,978,067 | A | 12/1990 | Berger et al. |
| 4,988,883 | A | 1/1991 | Oppawsky |
| 4,997,652 | A | 3/1991 | Wong et al. |
| 5,002,067 | A | 3/1991 | Berthelsen et al. |
| 5,002,582 | A | 3/1991 | Guire et al. |
| 5,003,992 | A | 4/1991 | Holleman et al. |
| 5,036,634 | A | 8/1991 | Lessard et al. |
| 5,041,089 | A | 8/1991 | Mueller et al. |
| 5,049,404 | A | 9/1991 | Kisler et al. |
| 5,069,940 | A | 12/1991 | Wenrick |
| 5,071,337 | A | 12/1991 | Heller et al. |
| 5,076,285 | A | 12/1991 | Hess et al. |
| 5,076,974 | A | 12/1991 | Modrek et al. |
| 5,087,246 | A | 2/1992 | Smith |
| 5,090,084 | A | 2/1992 | De |
| 5,098,443 | A | 3/1992 | Parel et al. |
| 5,102,402 | A | 4/1992 | Dror et al. |
| 5,114,719 | A | 5/1992 | Sabel et al. |
| 5,120,312 | A | 6/1992 | Wigness et al. |
| 5,164,188 | A | 11/1992 | Wong |
| 5,183,509 | A | 2/1993 | Brown et al. |
| 5,207,343 | A | 5/1993 | Bogadi |
| 5,219,120 | A | 6/1993 | Ehrenberg et al. |
| 5,219,690 | A | 6/1993 | Hammond |
| 5,221,698 | A | 6/1993 | Amiden et al. |
| 5,229,128 | A | 7/1993 | Haddad et al. |
| 5,246,867 | A | 9/1993 | Maliwal et al. |
| 5,248,752 | A | 9/1993 | Argyropoulos et al. |
| 5,254,164 | A | 10/1993 | Masahumi |
| 5,255,693 | A | 10/1993 | Dutcher et al. |
| 5,300,108 | A | 4/1994 | Rebell et al. |
| 5,300,114 | A | 4/1994 | Gwon |
| 5,304,121 | A | 4/1994 | Sahatjian |
| 5,310,559 | A | 5/1994 | Shah et al. |
| 5,314,419 | A | 5/1994 | Pelling et al. |
| 5,318,587 | A | 6/1994 | Davey |
| 5,324,325 | A | 6/1994 | Moaddeb |
| 5,344,298 | A | 9/1994 | Hull |
| 5,364,343 | A | 11/1994 | Apolet et al. |
| 5,372,577 | A | 12/1994 | Ungerleider |
| 5,378,475 | A | 1/1995 | Smith et al. |
| 5,382,234 | A | 1/1995 | Cornelius et al. |
| 5,385,148 | A | 1/1995 | Lesh et al. |
| 5,387,247 | A | 2/1995 | Vallana et al. |
| 5,395,618 | A | 3/1995 | Darougar et al. |
| 5,405,376 | A | 4/1995 | Mulier et al. |
| 5,405,631 | A | 4/1995 | Rosenthal |
| 5,410,773 | A | 5/1995 | Forkner |
| 5,413,638 | A | 5/1995 | Bernstein, Jr. et al. |
| 5,414,075 | A | 5/1995 | Swan et al. |
| 5,421,979 | A | 6/1995 | Stevenson |
| 5,423,777 | A | 6/1995 | Tajiri et al. |
| 5,431,649 | A | 7/1995 | Mulier et al. |
| 5,437,656 | A | 8/1995 | Shikani et al. |
| 5,443,505 | A | 8/1995 | Wong et al. |
| 5,447,724 | A | 9/1995 | Helmus et al. |
| 5,449,382 | A | 9/1995 | Dayton |
| 5,464,650 | A | 11/1995 | Berg et al. |
| 5,466,233 | A | 11/1995 | Weiner et al. |
| 5,472,436 | A | 12/1995 | Fremstad |
| 5,476,511 | A | 12/1995 | Gwon et al. |
| 5,501,735 | A | 3/1996 | Pender |
| 5,501,856 | A | 3/1996 | Ohtori et al. |
| 5,512,055 | A | 4/1996 | Domb et al. |
| 5,525,348 | A | 6/1996 | Whitbourne et al. |
| 5,527,389 | A | 6/1996 | Rosenblum et al. |
| 5,545,208 | A | 8/1996 | Wolff et al. |
| 5,556,633 | A | 9/1996 | Haddad et al. |
| 5,571,089 | A | 11/1996 | Crocker |
| 5,578,075 | A | 11/1996 | Dayton |
| 5,582,616 | A | 12/1996 | Bolduc et al. |
| 5,591,227 | A | 1/1997 | Dinh et al. |

(56) References Cited

U.S. PATENT DOCUMENTS

| | | |
|---|---|---|
| 5,605,696 A | 2/1997 | Eury et al. |
| 5,609,629 A | 3/1997 | Fearnot et al. |
| 5,618,568 A | 4/1997 | Seckora et al. |
| 5,624,411 A | 4/1997 | Tuch |
| 5,624,975 A | 4/1997 | Valencia |
| 5,626,919 A | 5/1997 | Chapman et al. |
| 5,630,879 A | 5/1997 | Eichmann et al. |
| 5,637,113 A | 6/1997 | Tartaglia et al. |
| 5,637,460 A | 6/1997 | Swan et al. |
| 5,643,362 A | 7/1997 | Garves |
| 5,645,592 A | 7/1997 | Nicolais et al. |
| 5,651,986 A | 7/1997 | Brem |
| 5,656,332 A | 8/1997 | Saito et al. |
| 5,658,387 A | 8/1997 | Reardon et al. |
| 5,673,473 A | 10/1997 | Johnson et al. |
| 5,679,400 A | 10/1997 | Tuch |
| 5,714,360 A | 2/1998 | Swan et al. |
| 5,725,493 A | 3/1998 | Avery et al. |
| 5,743,964 A | 4/1998 | Pankake |
| 5,766,242 A | 6/1998 | Wong et al. |
| 5,773,019 A | 6/1998 | Ashton et al. |
| 5,776,101 A | 7/1998 | Goy |
| 5,788,772 A | 8/1998 | Kunieda et al. |
| 5,807,331 A | 9/1998 | Den Heijer et al. |
| 5,807,395 A | 9/1998 | Mulier et al. |
| 5,810,836 A | 9/1998 | Hussein et al. |
| 5,824,072 A | 10/1998 | Wong |
| 5,830,173 A | 11/1998 | Avery et al. |
| 5,833,715 A | 11/1998 | Vachon et al. |
| 5,833,891 A | 11/1998 | Subramaniam et al. |
| 5,837,008 A | 11/1998 | Berg et al. |
| 5,837,088 A | 11/1998 | Palmgren et al. |
| 5,837,313 A | 11/1998 | Ding et al. |
| 5,849,359 A | 12/1998 | Burns et al. |
| 5,858,435 A | 1/1999 | Gallo |
| 5,868,697 A | 2/1999 | Richter et al. |
| 5,877,224 A | 3/1999 | Brocchini et al. |
| 5,882,336 A | 3/1999 | Janacek |
| 5,882,405 A | 3/1999 | Kish et al. |
| 5,886,026 A | 3/1999 | Hunter et al. |
| 5,897,911 A | 4/1999 | Loeffler |
| 5,904,144 A | 5/1999 | Hammage et al. |
| 5,913,653 A | 6/1999 | Kempf |
| 5,921,982 A | 7/1999 | Lesh et al. |
| 5,925,885 A | 7/1999 | Clark et al. |
| 5,928,662 A | 7/1999 | Phillips |
| 5,972,027 A | 10/1999 | Johnson |
| 5,972,369 A | 10/1999 | Roorda et al. |
| 5,976,256 A | 11/1999 | Kawano |
| 5,980,972 A | 11/1999 | Ding |
| 5,989,579 A | 11/1999 | Darougar et al. |
| 5,992,568 A | 11/1999 | Craig et al. |
| 5,997,517 A | 12/1999 | Whitbourne |
| 6,001,386 A | 12/1999 | Ashton et al. |
| 6,001,425 A | 12/1999 | Stash et al. |
| 6,019,784 A | 2/2000 | Hines |
| 6,033,582 A | 3/2000 | Lee et al. |
| 6,053,924 A | 4/2000 | Hussein |
| 6,056,998 A | 5/2000 | Fujimoto |
| 6,070,697 A | 6/2000 | Millard |
| 6,074,661 A | 6/2000 | Olejnik et al. |
| 6,091,978 A | 7/2000 | Johnson et al. |
| 6,094,887 A | 8/2000 | Swank et al. |
| 6,096,070 A | 8/2000 | Ragheb et al. |
| 6,099,562 A | 8/2000 | Ding et al. |
| 6,102,887 A | 8/2000 | Altman |
| 6,110,483 A | 8/2000 | Whitbourne et al. |
| 6,117,456 A | 9/2000 | Lee et al. |
| 6,120,536 A | 9/2000 | Ding et al. |
| 6,129,933 A | 10/2000 | Oshiack et al. |
| 6,143,037 A | 11/2000 | Goldstein et al. |
| 6,153,252 A | 11/2000 | Hossainy et al. |
| 6,156,373 A | 12/2000 | Zhong et al. |
| 6,156,526 A | 12/2000 | Newman |
| 6,165,526 A | 12/2000 | Newman et al. |
| 6,177,095 B1 | 1/2001 | Sawhney et al. |
| 6,187,370 B1 | 2/2001 | Dinh et al. |
| 6,190,077 B1 | 2/2001 | Newson et al. |
| 6,197,324 B1 | 3/2001 | Crittenden |
| 6,203,551 B1 | 3/2001 | Wu |
| 6,203,556 B1 | 3/2001 | Evans et al. |
| 6,203,732 B1 | 3/2001 | Clubb et al. |
| 6,207,337 B1 | 3/2001 | Swain |
| 6,212,434 B1 | 4/2001 | Scheiner et al. |
| 6,214,008 B1 | 4/2001 | Illi |
| 6,214,115 B1 | 4/2001 | Taylor et al. |
| 6,214,901 B1 | 4/2001 | Chudzik et al. |
| 6,217,895 B1 | 4/2001 | Guo et al. |
| 6,218,016 B1 | 4/2001 | Tedeschi |
| 6,245,089 B1 | 6/2001 | Daniel et al. |
| 6,245,099 B1 | 6/2001 | Edwin et al. |
| 6,248,112 B1 | 6/2001 | Gambale et al. |
| 6,251,090 B1 | 6/2001 | Avery et al. |
| 6,251,136 B1 | 6/2001 | Guruwaiya et al. |
| 6,251,418 B1 | 6/2001 | Ahern et al. |
| 6,254,921 B1 | 7/2001 | Chappa et al. |
| 6,278,018 B1 | 8/2001 | Swan |
| 6,279,505 B1 | 8/2001 | Plester et al. |
| 6,287,285 B1 | 9/2001 | Michal et al. |
| 6,290,728 B1 | 9/2001 | Phelps et al. |
| 6,298,272 B1 | 10/2001 | Peterfeso et al. |
| 6,303,148 B1 | 10/2001 | Hennink et al. |
| 6,306,125 B1 | 10/2001 | Parker et al. |
| 6,306,426 B1 | 10/2001 | Olejnik et al. |
| 6,309,370 B1 | 10/2001 | Haim et al. |
| 6,322,847 B1 | 11/2001 | Zhong et al. |
| RE37,463 E | 12/2001 | Altman |
| 6,331,313 B1 | 12/2001 | Wong et al. |
| 6,333,595 B1 | 12/2001 | Horikawa et al. |
| 6,344,035 B1 | 2/2002 | Chudzik et al. |
| 6,345,630 B2 | 2/2002 | Fishkin et al. |
| 6,358,247 B1 | 3/2002 | Altman et al. |
| 6,358,556 B1 | 3/2002 | Ding et al. |
| 6,360,129 B1 | 3/2002 | Ley et al. |
| 6,368,658 B1 | 4/2002 | Schwarz et al. |
| 6,375,972 B1 | 4/2002 | Guo et al. |
| 6,394,995 B1 | 5/2002 | Solar et al. |
| 6,395,326 B1 | 5/2002 | Castro et al. |
| 6,399,144 B2 | 6/2002 | Dinh et al. |
| 6,399,655 B1 | 6/2002 | De et al. |
| 6,399,704 B1 | 6/2002 | Laurin et al. |
| 6,406,754 B2 | 6/2002 | Chappa et al. |
| 6,431,770 B1 | 8/2002 | Kurematsu et al. |
| 6,435,959 B1 | 8/2002 | Skrmetta |
| 6,451,373 B1 | 9/2002 | Hossainy et al. |
| 6,478,776 B1 | 11/2002 | Roseman et al. |
| 6,497,691 B1 | 12/2002 | Bevins et al. |
| 6,501,994 B1 | 12/2002 | Janke et al. |
| 6,505,082 B1 | 1/2003 | Scheiner et al. |
| 6,506,411 B2 | 1/2003 | Hunter et al. |
| 6,506,437 B1 | 1/2003 | Harish et al. |
| 6,517,515 B1 | 2/2003 | Eidenschink |
| 6,517,889 B1 | 2/2003 | Jayaraman |
| 6,521,299 B1 | 2/2003 | Dessauer |
| 6,527,863 B1 | 3/2003 | Pacetti et al. |
| 6,534,112 B1 * | 3/2003 | Bouchier ............... A61L 27/54 |
| | | 427/430.1 |
| 6,544,544 B2 | 4/2003 | Hunter et al. |
| 6,544,582 B1 | 4/2003 | Yoe |
| 6,547,787 B1 | 4/2003 | Altman et al. |
| 6,548,078 B2 | 4/2003 | Guo et al. |
| 6,555,157 B1 | 4/2003 | Hossainy |
| 6,559,560 B1 | 5/2003 | Jin et al. |
| 6,562,051 B1 | 5/2003 | Bolduc et al. |
| 6,562,136 B1 | 5/2003 | Chappa et al. |
| 6,565,659 B1 | 5/2003 | Pacetti et al. |
| 6,572,644 B1 | 6/2003 | Moein |
| 6,585,764 B2 | 7/2003 | Wright et al. |
| 6,595,958 B1 | 7/2003 | Mickley |
| 6,599,560 B1 | 7/2003 | Daggett et al. |
| 6,605,154 B1 | 8/2003 | Villareal |
| 6,607,598 B2 | 8/2003 | Schwarz et al. |
| 6,613,017 B1 | 9/2003 | Mickley |
| 6,616,765 B1 | 9/2003 | Castro et al. |

(56) References Cited

U.S. PATENT DOCUMENTS

| | | |
|---|---|---|
| 6,623,504 B2 | 9/2003 | Vrba et al. |
| 6,653,426 B2 | 11/2003 | Alvarado et al. |
| 6,656,529 B1 | 12/2003 | Pankake |
| 6,669,980 B2 | 12/2003 | Hansen |
| 6,669,994 B2 | 12/2003 | Swan et al. |
| 6,673,154 B1 | 1/2004 | Pacetti et al. |
| 6,676,987 B2 | 1/2004 | Zhong et al. |
| 6,695,920 B1 | 2/2004 | Pacetti et al. |
| 6,706,023 B1 | 3/2004 | Huttner et al. |
| 6,709,514 B1 | 3/2004 | Hossainy |
| 6,709,712 B2 | 3/2004 | Chappa et al. |
| 6,713,081 B2 | 3/2004 | Robinson et al. |
| 6,716,081 B2 | 4/2004 | Kim et al. |
| 6,716,196 B2 | 4/2004 | Lesh et al. |
| 6,719,750 B2 | 4/2004 | Varner et al. |
| 6,719,805 B1 | 4/2004 | Ahern |
| 6,723,373 B1 | 4/2004 | Narayanan et al. |
| 6,725,901 B1 | 4/2004 | Kramer et al. |
| 6,726,918 B1 | 4/2004 | Wong et al. |
| 6,743,233 B1 | 6/2004 | Baldwin et al. |
| 6,743,462 B1 | 6/2004 | Pacetti |
| 6,743,463 B2 | 6/2004 | Weber et al. |
| 6,752,959 B2 | 6/2004 | Smith et al. |
| 6,764,470 B2 | 7/2004 | Dimick |
| 6,783,793 B1 | 8/2004 | Hossainy et al. |
| 6,803,070 B2 | 10/2004 | Weber |
| 6,818,063 B1 | 11/2004 | Kerrigan |
| 6,896,842 B1 | 5/2005 | Hamilton et al. |
| 6,941,632 B1 | 9/2005 | Mead et al. |
| 6,981,982 B2 | 1/2006 | Armstrong et al. |
| 7,010,933 B2 | 3/2006 | Ishitomi et al. |
| 7,041,174 B2 | 5/2006 | Carlson et al. |
| 7,045,015 B2 | 5/2006 | Renn et al. |
| 7,077,848 B1 | 7/2006 | De Juan, Jr. et al. |
| 7,077,910 B2 | 7/2006 | Chappa et al. |
| 7,087,658 B2 | 8/2006 | Swan et al. |
| 7,090,421 B1 | 8/2006 | Mead et al. |
| 7,105,350 B2 | 9/2006 | Foster et al. |
| 7,125,577 B2 | 10/2006 | Chappa |
| 7,163,523 B2 | 1/2007 | Devens, Jr. et al. |
| 7,186,374 B2 | 3/2007 | Zelina et al. |
| 7,192,484 B2 | 3/2007 | Chappa et al. |
| 7,198,675 B2 | 4/2007 | Fox et al. |
| 7,335,314 B2 | 2/2008 | Wu |
| 7,563,324 B1 | 7/2009 | Chen et al. |
| 7,597,764 B2 * | 10/2009 | Verlee .................. A61P 31/04 |
| | | 118/667 |
| 7,611,532 B2 | 11/2009 | Bates et al. |
| 7,638,156 B1 | 12/2009 | Kokish et al. |
| 7,669,548 B2 | 3/2010 | Chappa |
| 7,743,727 B2 | 6/2010 | Shekalim |
| 7,806,612 B1 | 10/2010 | Wangler |
| 7,883,749 B2 | 2/2011 | Carlson |
| 7,958,840 B2 | 6/2011 | Chappa |
| 8,003,156 B2 | 8/2011 | Van Sciver |
| 8,166,909 B2 | 5/2012 | Chappa |
| 8,171,595 B1 | 5/2012 | Umhoefer, Jr. et al. |
| 8,246,974 B2 | 8/2012 | Chappa |
| 8,282,981 B2 | 10/2012 | Andreacchi et al. |
| 8,318,263 B2 | 11/2012 | Carlson et al. |
| D676,975 S | 2/2013 | Bickford |
| 8,632,837 B2 | 1/2014 | Gong et al. |
| 8,844,543 B2 | 9/2014 | Bickford et al. |
| 8,889,760 B2 | 11/2014 | Kurdyumov et al. |
| 8,961,054 B2 | 2/2015 | Gilbert et al. |
| 8,974,134 B2 | 3/2015 | Wilson et al. |
| 9,205,447 B2 | 12/2015 | Wilson |
| 9,283,350 B2 | 3/2016 | Chappa et al. |
| 9,308,355 B2 | 4/2016 | Chappa et al. |
| 9,364,349 B2 | 6/2016 | Chappa et al. |
| 9,623,215 B2 | 4/2017 | Chappa et al. |
| 9,827,401 B2 | 11/2017 | Chappa et al. |
| 10,022,476 B2 * | 7/2018 | Zhang ................ A61M 25/0009 |
| 10,080,819 B2 * | 9/2018 | Gross .................. A61L 27/54 |
| 10,099,041 B2 | 10/2018 | Chappa et al. |
| 10,441,679 B2 * | 10/2019 | Gross .................. A61L 27/46 |
| 10,507,309 B2 | 12/2019 | Chappa et al. |
| 11,628,466 B2 | 4/2023 | Chappa et al. |
| 2001/0001824 A1 | 5/2001 | Wu |
| 2001/0014717 A1 | 8/2001 | Hossainy et al. |
| 2001/0022988 A1 | 9/2001 | Schwarz et al. |
| 2001/0026834 A1 | 10/2001 | Chappa et al. |
| 2001/0029351 A1 | 10/2001 | Falotico et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0013298 A1 | 1/2002 | Hunter |
| 2002/0018795 A1 | 2/2002 | Whitbourne et al. |
| 2002/0026176 A1 | 2/2002 | Varner et al. |
| 2002/0026236 A1 | 2/2002 | Helmus et al. |
| 2002/0032434 A1 | 3/2002 | Chudzik et al. |
| 2002/0032477 A1 | 3/2002 | Helmus et al. |
| 2002/0046521 A1 | 4/2002 | Steinacker, Sr. et al. |
| 2002/0051730 A1 | 5/2002 | Bodnar et al. |
| 2002/0054900 A1 | 5/2002 | Kamath et al. |
| 2002/0062730 A1 | 5/2002 | Thornton |
| 2002/0082679 A1 | 6/2002 | Sirhan et al. |
| 2002/0091433 A1 | 7/2002 | Ding et al. |
| 2002/0094440 A1 | 7/2002 | Llanos et al. |
| 2002/0103526 A1 | 8/2002 | Steinke |
| 2002/0107330 A1 | 8/2002 | Pinchuk et al. |
| 2002/0111590 A1 | 8/2002 | Davila et al. |
| 2002/0114823 A1 | 8/2002 | Sirhan et al. |
| 2002/0115400 A1 | 8/2002 | Skrmetta |
| 2002/0120326 A1 | 8/2002 | Michal |
| 2002/0133183 A1 | 9/2002 | Lentz et al. |
| 2002/0138048 A1 | 9/2002 | Tuch |
| 2002/0155212 A1 | 10/2002 | Hossainy |
| 2002/0159915 A1 | 10/2002 | Zelina et al. |
| 2002/0165265 A1 | 11/2002 | Hunter et al. |
| 2002/0168394 A1 | 11/2002 | Hossainy et al. |
| 2002/0188037 A1 | 12/2002 | Chudzik et al. |
| 2002/0188170 A1 | 12/2002 | Santamore et al. |
| 2002/0198511 A1 | 12/2002 | Varner et al. |
| 2003/0003221 A1 | 1/2003 | Zhong et al. |
| 2003/0004209 A1 | 1/2003 | Hunter et al. |
| 2003/0014036 A1 | 1/2003 | Varner et al. |
| 2003/0021828 A1 | 1/2003 | Guo et al. |
| 2003/0031780 A1 | 2/2003 | Chudzik et al. |
| 2003/0039689 A1 | 2/2003 | Chen et al. |
| 2003/0044514 A1 | 3/2003 | Richard |
| 2003/0054023 A1 | 3/2003 | Hughes et al. |
| 2003/0054090 A1 | 3/2003 | Hansen |
| 2003/0059520 A1 | 3/2003 | Chen et al. |
| 2003/0059920 A1 | 3/2003 | Drohan et al. |
| 2003/0060783 A1 | 3/2003 | Koole et al. |
| 2003/0065332 A1 | 4/2003 | Tenhuisen et al. |
| 2003/0083646 A1 | 5/2003 | Sirhan et al. |
| 2003/0088307 A1 | 5/2003 | Shulze et al. |
| 2003/0094736 A1 | 5/2003 | Qin et al. |
| 2003/0096131 A1 | 5/2003 | Beavers |
| 2003/0113439 A1 | 6/2003 | Pacetti et al. |
| 2003/0120200 A1 | 6/2003 | Bergheim et al. |
| 2003/0143315 A1 | 7/2003 | Pui et al. |
| 2003/0150380 A1 | 8/2003 | Yoe |
| 2003/0152693 A1 | 8/2003 | Su et al. |
| 2003/0157187 A1 | 8/2003 | Hunter |
| 2003/0157241 A1 | 8/2003 | Hossainy et al. |
| 2003/0158598 A1 | 8/2003 | Ashton et al. |
| 2003/0161937 A1 | 8/2003 | Leiby et al. |
| 2003/0165613 A1 | 9/2003 | Chappa et al. |
| 2003/0175324 A1 | 9/2003 | Robinson et al. |
| 2003/0181848 A1 | 9/2003 | Bergheim et al. |
| 2003/0190420 A1 | 10/2003 | Chappa et al. |
| 2003/0207856 A1 | 11/2003 | Tremble et al. |
| 2003/0215564 A1 | 11/2003 | Heller et al. |
| 2003/0229333 A1 | 12/2003 | Ashton et al. |
| 2003/0232087 A1 | 12/2003 | Lawin et al. |
| 2003/0232122 A1 | 12/2003 | Chappa et al. |
| 2003/0236513 A1 | 12/2003 | Schwarz et al. |
| 2003/0236514 A1 | 12/2003 | Schwarz |
| 2004/0006146 A1 | 1/2004 | Evans et al. |
| 2004/0022853 A1 | 2/2004 | Ashton et al. |

(56) References Cited

U.S. PATENT DOCUMENTS

| | | |
|---|---|---|
| 2004/0034357 A1 | 2/2004 | Beane et al. |
| 2004/0037886 A1 | 2/2004 | Hsu |
| 2004/0044404 A1 | 3/2004 | Stucke et al. |
| 2004/0047911 A1 | 3/2004 | Lyu et al. |
| 2004/0062592 A1 | 4/2004 | Shekalim et al. |
| 2004/0062875 A1 | 4/2004 | Chappa et al. |
| 2004/0073298 A1 | 4/2004 | Hossainy |
| 2004/0081745 A1 | 4/2004 | Hansen |
| 2004/0111818 A1 | 6/2004 | Ma |
| 2004/0121014 A1 | 6/2004 | Guo et al. |
| 2004/0133155 A1 | 7/2004 | Varner et al. |
| 2004/0137059 A1 | 7/2004 | Nivaggioli et al. |
| 2004/0142013 A1 | 7/2004 | Rubsamen |
| 2004/0143314 A1 | 7/2004 | Sommer et al. |
| 2004/0161547 A1 | 8/2004 | Carlson et al. |
| 2004/0185168 A1 | 9/2004 | Weber et al. |
| 2004/0194704 A1 | 10/2004 | Chappa et al. |
| 2004/0211362 A1 | 10/2004 | Castro et al. |
| 2004/0213893 A1 | 10/2004 | Boulais |
| 2005/0015142 A1 | 1/2005 | Austin et al. |
| 2005/0019371 A1 | 1/2005 | Anderson et al. |
| 2005/0059956 A1 | 3/2005 | Varner et al. |
| 2005/0098097 A1 | 5/2005 | Chen et al. |
| 2005/0129732 A1 | 6/2005 | Rubsamen |
| 2005/0142070 A1 | 6/2005 | Hartley |
| 2005/0143363 A1 | 6/2005 | De Juan et al. |
| 2005/0147690 A1 | 7/2005 | Masters et al. |
| 2005/0158449 A1 | 7/2005 | Chappa |
| 2005/0196518 A1 | 9/2005 | Stenzel et al. |
| 2005/0233061 A1 | 10/2005 | Schwarz et al. |
| 2005/0233062 A1 | 10/2005 | Hossainy et al. |
| 2005/0240147 A1 | 10/2005 | Makower et al. |
| 2005/0255142 A1 | 11/2005 | Chudzik et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0281863 A1 | 12/2005 | Anderson et al. |
| 2005/0287188 A1 | 12/2005 | Anderson et al. |
| 2006/0020295 A1 | 1/2006 | Brockway et al. |
| 2006/0029720 A1 | 2/2006 | Panos et al. |
| 2006/0045981 A1 | 3/2006 | Tsushi et al. |
| 2006/0059520 A1 | 3/2006 | Miyazawa et al. |
| 2006/0064134 A1 | 3/2006 | Mazar et al. |
| 2006/0064142 A1 | 3/2006 | Chavan et al. |
| 2006/0074404 A1 | 4/2006 | Struble |
| 2006/0088653 A1 | 4/2006 | Chappa |
| 2006/0096535 A1 | 5/2006 | Haller et al. |
| 2006/0110428 A1 | 5/2006 | De Juan et al. |
| 2006/0111754 A1 | 5/2006 | Rezai et al. |
| 2006/0116590 A1 | 6/2006 | Fayram et al. |
| 2006/0165872 A1 | 7/2006 | Chappa et al. |
| 2006/0191476 A1 | 8/2006 | Nagase et al. |
| 2006/0269663 A1 | 11/2006 | Mori et al. |
| 2007/0065481 A1 | 3/2007 | Chudzik et al. |
| 2007/0101933 A1 | 5/2007 | Chappa |
| 2007/0116855 A1 | 5/2007 | Fox et al. |
| 2007/0131165 A1 | 6/2007 | Fox et al. |
| 2007/0141232 A1 | 6/2007 | Tochterman et al. |
| 2007/0259100 A1 | 11/2007 | Guerriero et al. |
| 2007/0259102 A1 | 11/2007 | Mcniven et al. |
| 2007/0259125 A1 | 11/2007 | O'brien et al. |
| 2007/0275175 A1 | 11/2007 | Hossainy |
| 2008/0149025 A1 | 6/2008 | Swenson |
| 2008/0179781 A1 | 7/2008 | Iwata |
| 2008/0274266 A1 | 11/2008 | Davis et al. |
| 2009/0018643 A1 | 1/2009 | Hashi et al. |
| 2009/0054837 A1 | 2/2009 | Von Holst et al. |
| 2009/0084311 A1 | 4/2009 | Yoshida et al. |
| 2009/0090299 A1 | 4/2009 | Menendez et al. |
| 2009/0176030 A1 | 7/2009 | Carlson et al. |
| 2009/0269481 A1 | 10/2009 | Chappa et al. |
| 2009/0317537 A1 | 12/2009 | Andreacchi |
| 2010/0040766 A1 | 2/2010 | Chappa et al. |
| 2010/0055294 A1 | 3/2010 | Wang et al. |
| 2010/0070020 A1 | 3/2010 | Hashi et al. |
| 2010/0179475 A1 | 7/2010 | Hoffmann et al. |
| 2010/0227044 A1 | 9/2010 | Scheer |
| 2010/0272774 A1 | 10/2010 | Chappa |
| 2010/0319183 A1 | 12/2010 | Hulseman et al. |
| 2011/0046724 A1 | 2/2011 | Heilmann et al. |
| 2011/0104392 A1 | 5/2011 | Carlson et al. |
| 2011/0151199 A1 | 6/2011 | Nelson et al. |
| 2011/0238011 A1 | 9/2011 | Scheller et al. |
| 2011/0253170 A1 | 10/2011 | Clark et al. |
| 2011/0281019 A1 | 11/2011 | Gong et al. |
| 2011/0281020 A1 | 11/2011 | Gong et al. |
| 2011/0311713 A1 | 12/2011 | O'neill et al. |
| 2011/0311764 A1 | 12/2011 | Hulseman et al. |
| 2012/0025145 A1 | 2/2012 | Tokumoto et al. |
| 2012/0043693 A1 | 2/2012 | King et al. |
| 2012/0059317 A1 | 3/2012 | Michiyo et al. |
| 2012/0100279 A1 | 4/2012 | Neumann et al. |
| 2012/0258246 A1 | 10/2012 | Saine et al. |
| 2012/0315376 A1 | 12/2012 | Nguyen et al. |
| 2013/0337147 A1 | 12/2013 | Chappa et al. |
| 2014/0121597 A1 | 5/2014 | Chappa et al. |
| 2014/0161964 A1 | 6/2014 | Chappa et al. |
| 2014/0328998 A1 | 11/2014 | Chappa et al. |
| 2015/0017429 A1 | 1/2015 | Li et al. |
| 2015/0044376 A1 | 2/2015 | Topf et al. |
| 2016/0256668 A1 | 9/2016 | Chappa et al. |
| 2016/0271644 A1 | 9/2016 | Weinmann et al. |
| 2018/0036519 A1 | 2/2018 | Chappa et al. |
| 2018/0110903 A1 | 4/2018 | Slager et al. |
| 2019/0099778 A1 | 4/2019 | Antoniazzi |
| 2019/0143661 A1 | 5/2019 | Hunt et al. |
| 2019/0151629 A1 | 5/2019 | Chappa et al. |
| 2019/0216985 A1* | 7/2019 | McBurney ............ A61L 27/505 |
| 2020/0171531 A1 | 6/2020 | Chappa et al. |
| 2020/0246604 A1* | 8/2020 | Asefi ................... A61L 29/16 |
| 2020/0353502 A1 | 11/2020 | Ko et al. |
| 2020/0360572 A1* | 11/2020 | Militello ................. B05C 21/00 |
| 2021/0030397 A1* | 2/2021 | Lee ....................... A61B 8/4455 |
| 2021/0220866 A1* | 7/2021 | Chappa ............... B05C 11/1026 |
| 2021/0386917 A1* | 12/2021 | Burgmeier ........... A61K 31/337 |

FOREIGN PATENT DOCUMENTS

| | | |
|---|---|---|
| DE | 20200223 | 4/2002 |
| DE | 10053826 | 5/2002 |
| EP | 0096433 | 12/1983 |
| EP | 0144873 | 6/1985 |
| EP | 0414233 | 2/1991 |
| EP | 0604022 | 6/1994 |
| EP | 0623354 | 11/1994 |
| EP | 0716836 | 6/1996 |
| EP | 0734721 | 10/1996 |
| EP | 0747069 | 12/1996 |
| EP | 0857516 | 2/1998 |
| EP | 0832655 | 4/1998 |
| EP | 0834282 | 4/1998 |
| EP | 0945148 | 9/1999 |
| EP | 0879595 | 1/2003 |
| EP | 1374924 | 1/2004 |
| EP | 1382302 | 1/2004 |
| EP | 1594623 | 4/2007 |
| EP | 0923953 | 8/2008 |
| EP | 1610836 | 8/2008 |
| EP | 3549679 | 10/2019 |
| FR | 1304457 | 8/1962 |
| FR | 2733163 | 10/1996 |
| GB | 525373 | 8/1940 |
| GB | 757659 | 9/1956 |
| GB | 2301296 | 12/1996 |
| GB | 104464 | 4/2001 |
| JP | 57048354 | 3/1982 |
| JP | 63-011547 | 1/1988 |
| JP | 02-036882 | 2/1990 |
| JP | H0262550 | 3/1990 |
| JP | H03021367 | 1/1991 |
| JP | 09-038546 | 2/1997 |
| JP | 09-194347 | 7/1997 |
| JP | 2003039015 | 2/2003 |
| JP | 2005059225 | 3/2005 |

(56) References Cited

FOREIGN PATENT DOCUMENTS

| | | |
|---|---|---|
| JP | 06-246207 | 9/2006 |
| JP | 08-086466 | 4/2008 |
| JP | 2015527092 | 9/2015 |
| JP | 2016504058 | 2/2016 |
| JP | 6445532 | 12/2018 |
| WO | 1989005664 | 6/1989 |
| WO | 1991012779 | 9/1991 |
| WO | 1992011895 | 7/1992 |
| WO | 1992015286 | 9/1992 |
| WO | 1993000174 | 1/1993 |
| WO | 1993015682 | 8/1993 |
| WO | 1994021308 | 9/1994 |
| WO | 1994021309 | 9/1994 |
| WO | 1995003036 | 2/1995 |
| WO | 1997010011 | 3/1997 |
| WO | 1997037640 | 11/1997 |
| WO | 1998017331 | 4/1998 |
| WO | 1998032474 | 7/1998 |
| WO | 1999001114 | 1/1999 |
| WO | 1998058690 | 3/1999 |
| WO | 1999036071 | 7/1999 |
| WO | 1999038546 | 8/1999 |
| WO | 1999055396 | 11/1999 |
| WO | 2000001322 | 1/2000 |
| WO | 2000002564 | 1/2000 |
| WO | 2000012163 | 3/2000 |
| WO | 2000021584 | 4/2000 |
| WO | 2001021326 | 3/2001 |
| WO | 2001032382 | 5/2001 |
| WO | 2001078626 | 10/2001 |
| WO | 2001094103 | 12/2001 |
| WO | 2002009786 | 2/2002 |
| WO | 2002020174 | 3/2002 |
| WO | 2003004072 | 1/2003 |
| WO | 2003024615 | 3/2003 |
| WO | 2004028579 | 4/2004 |
| WO | 2004028699 | 4/2004 |
| WO | 2004037126 | 5/2004 |
| WO | 2004037443 | 5/2004 |
| WO | 2004073885 | 9/2004 |
| WO | 2004091682 | 10/2004 |
| WO | 2004098565 | 11/2004 |
| WO | 2005009297 | 2/2005 |
| WO | 2006110366 | 10/2006 |
| WO | 2007059144 | 5/2007 |
| WO | 2007100801 | 9/2007 |
| WO | 2008002357 | 1/2008 |
| WO | 2009132214 | 10/2009 |
| WO | 2010024898 | 3/2010 |
| WO | 2010146096 | 12/2010 |
| WO | 2013181498 | 12/2013 |
| WO | 2014066760 | 5/2014 |
| WO | 2014182833 | 11/2014 |
| WO | 2020112816 | 6/2020 |

OTHER PUBLICATIONS

"Communication Pursuant to Article 94(3) EPC," for European Patent Application No. 13729853.5 dated Apr. 30, 2018 (6 pages).
"Communication Pursuant to Article 94(3) EPC," for European Patent Application No. 13792526.9 dated Apr. 19, 2018 (5 pages).
"Communication Pursuant to Article 94(3) EPC," for European Patent Application No. 13792526.9 dated Aug. 6, 2019 (5 pages).
"Communication Pursuant to Article 94(3) EPC," for European Patent Application No. 13792526.9 dated Nov. 29, 2018 (4 pages).
"Communication Pursuant to Rule 164(2)(b) and Article 94(3) EPC," for European Patent Application No. 14730319.2 dated Sep. 4, 2017 (12 pages).
"Communication Pursuant to Rules 161 and 162 EPC," for European Patent Application No. 13729853.5, dated Feb. 13, 2015 (2 pages).
"Communication Pursuant to Rules 161(1) and 162 EPC," for European Application No. 13792526.9, dated Jul. 7, 2015 (2 pages).
"Communication Pursuant to Rules 161(1) and 162 EPC," for European Patent Application No. 14730319.2, dated Dec. 22, 2015 (2 pages).
"Complete File History," for U.S. Appl. No. 12/109,139 downloaded Dec. 18, 2017 (276 pages).
"Complete File History," for U.S. Appl. No. 13/906,599 downloaded Dec. 18, 2017 (249 pages).
"Complete File History," for U.S. Appl. No. 14/272,204 downloaded Dec. 18, 2017 (302 pages).
"Complete File History," for U.S. Appl. No. 15/061,234 downloaded Apr. 9, 2020 (118 pages).
"Complete File History," for U.S. Appl. No. 15/783,554 downloaded Apr. 9, 2020 (107 pages).
"Complete File History," for U.S. Appl. No. 16/160,425 downloaded Apr. 9, 2020 (131 pages).
"Cross-Link," http://en.wikipedia.org/wiki/Cross-link; retrieved Nov. 6, 2009 (4 pages).
Di Mario, et al., "Radioactive Stents—A Dead End?," Current Interventional Cardiology Reports, 2000 (2 pages), 87-88.
"European Examination Report," for European Application No. 04 711 809.6 dated Jan. 23, 2006 (4 pages).
"European Examination Report," for European Application No. 04 759 211.8 dated Aug. 7, 2006 (5 pages).
"European Examination Report," for European Application No. 06740366.7 dated Oct. 19, 2010 (4 pages).
"European Examination Report," for European Application No. 06740366.7, dated May 5, 2009 (4 pages).
"European Search Report," for European Patent Application No. 19174997.7 dated Sep. 10, 2019 (9 pages).
"Final Office Action," for Japanese Application No. 2006-509776, dated Jul. 5, 2011, (7 pages).
"Final Office Action," for Japanese Patent Application No. 2015-539837 dated Oct. 1, 2018 (7 pages) with English Translation.
"Final Rejection," for Japanese Patent Application No. 2015-515223 dated Nov. 22, 2017 (8 pages) with English translation.
"First Office Action," for CA Application No. 2604832, dated Mar. 16, 2012 (4 pages).
"First Office Action," for Japanese patent Application No. 2006-503609, dated Mar. 30, 2010 (7 pages) with English translation.
Hiemenz, Paul "Polymer Chemistry: The Basic Concepts," CRC Press, 1984 (pp. 9 and 12).
"International Preliminary Report on Patentability," for International Application No. PCT/US2005/038628 dated May 10, 2007 (10 pages).
"International Preliminary Report on Patentability," For PCT Application No. PCT/US2013/043547, dated Dec. 11, 2014 (7 pages).
"International Preliminary Report on Patentability," for PCT/US2013/066810, dated May 7, 2015 (12 pages).
"International Preliminary Report on Patentability," for PCT/US2014/037179 dated Nov. 19, 2015 (9 pages).
"International Preliminary Report on Patentability," from International Application No. PCT/US2004/004486, dated Aug. 19, 2005, (6 pages).
"International Search Report & Written Opinion," for PCT/US2004/010692, dated Jul. 23, 2004 (9 pages).
"International Search Report and Written Opinion," For International Application No. PCT/US2005/038628 dated Mar. 22, 2006 (16 pages).
"International Search Report and Written Opinion," For PCT Application No. PCT/US2014/037179 dated Feb. 19, 2015 (15 pages).
"International Search Report and Written Opinion," for PCT Application No. PCT/US2019/063311 dated Mar. 19, 2020 (13 pages).
"International Search Report and Written Opinion," for PCT/US2006/044218, dated Mar. 22, 2007 (12 pages).
"International Search Report and Written Opinion," for PCT/US2009/041575, dated Jul. 22, 2009 (15 pages).
"International Search Report and Written Opinion," for PCT/US2013/043547, dated Oct. 1, 2013 (10 pages).
"International Search Report and Written Opinion," for PCT/US2013/066810, dated Apr. 17, 2014 (18 pages).
"International Search Report," for PCT/US2004/004486, dated Jul. 19, 2004 (8 pages).

(56) References Cited

OTHER PUBLICATIONS

"Invitation to Pay Additional Fees and, Where Applicable, Protest Fee," for PCT/US2013/066810, mailed Feb. 7, 2014 (6 pages).
"Invitation to Pay Additional Fees," For PCT Application No. PCT/US2014/037179, mailed on Oct. 24, 2014 (5 pages).
"Non-Final Office Action," for U.S. Appl. No. 14/063,113 dated Nov. 4, 2020 (17 pages).
"Notice of Allowance Received," for Japanese Application No. 2006-509776, dated Dec. 1, 2011, (4 pages) including English translation.
"Office Action Response," for Canadian Patent Application No. 2,889,062 filed Mar. 9, 2020 (18 pages).
"Office Action Response," for Canadian Patent Application No. 2,889,062 filed Sep. 18, 2020 (11 pages).
"Office Action," for Canadian Patent Application No. 2,874,824 dated Apr. 11, 2019 (5 pages).
"Office Action," for Canadian Patent Application No. 2,874,824 dated Aug. 25, 2020 (3 pages).
"Office Action," for Canadian Patent Application No. 2,874,824 dated Jan. 9, 2020 (4 pages).
"Office Action," for Canadian Patent Application No. 2,889,062 dated Jun. 5, 2020 (3 pages).
"Office Action," for Canadian Patent Application No. 2,889,062 dated Sep. 12, 2019 (3 pages).
"Office Action," for Canadian Patent Application No. 2,911,482 dated Jul. 17, 2020 (3 pages).
"Office Action," for Japanese Patent Application No. 2015-515223 dated Feb. 21, 2019 (5 pages) with English Translation.
"Office Action," for Japanese Patent Application No. 2015-515223 dated Mar. 24, 2017 (10 pages) with English translation.
"Office Action," for Japanese Patent Application No. 2015-539837 dated Aug. 31, 2017 (11 pages) with English translation.
"Office Action," for Japanese Patent Application No. 2015-539837 dated Jun. 28, 2018 (7 pages) with English translation.
"Office Action," for Japanese Patent Application No. 2016-513047 dated Mar. 6, 2018 (11 pages) with English translation.
"Office Action," for Mexican Patent Application No. MX/a/2014/014574 dated Jun. 15, 2017 (1 page), English summary.
"Partial File History," for U.S. Appl. No. 14/063,113 downloaded Apr. 9, 2020 (409 pages).
"Response to Communication Pursuant to Article 94(3) EPC," for European Patent Application No. 13729853.5, filed with the EPO Sep. 6, 2018 (12 pages).
"Response to Communication Pursuant to Article 94(3) EPC," for European Patent Application No. 13792526.9 filed Dec. 3, 2019 (9 pages).
"Response to Communication Pursuant to Article 94(3) EPC," for European Patent Application No. 13792526.9 filed Mar. 13, 2019 (6 pages).
"Response to Communication Pursuant to Article 94(3) EPC," for European Patent Application No. 13792526.9 filed with the EPO Aug. 17, 2018 (60 pages).
"Response to Communication Pursuant to Rule 164(2)(b) and Article 94(3) EPC," for European Patent Application No. 14730319.2 filed with the EPO Jan. 2, 2018 (19 pages).
"Response to Communication Pursuant to Rules 161 and 162 EPC," for European Patent Application No. 13729853.5, filed with the EPO Aug. 13, 2015 (21 pages).
"Response to Communication Pursuant to Rules 161(1) and 162 EPC," for European Patent Application No. 13792526.9, dated Jul. 7, 2015 and filed with the EPO Jan. 7, 2016 (18 pages).
"Response to Communication Pursuant to Rules 161(1) and 162 EPC," for European Patent Application No. 14730319.2, filed with the EPO Jun. 24, 2016 (11 pages).
"Response to European Examination Report," for European Application No. 06740366.7, filed Feb. 22, 2011 (8 pages).
"Response to Office Action," for Canadian Patent Application No. 2,874,824 filed May 8, 2020 (15 pages).
"Response to Office Action," for Canadian Patent Application No. 2,874,824 filed Nov. 4, 2020 (6 pages).
"Response to Office Action," for Canadian Patent Application No. 2,874,824 filed Oct. 7, 2019 (18 pages).
"Response to Office Action," for Canadian Patent Application No. 2,911,482 filed Oct. 28, 2020 (10 pages).
"Response to Search Report," for European Patent Application No. 19174997.7 filed Mar. 31, 2020 (30 pages).
"Ultrasonic Spray Nozzle Systems," SONO-TEK Corporation Brochure, 2005 (16 pages).
Yeo, Yoon "A New Microencapsulation Method Using an Ultrasonic Atomizer Based on Interfacial Solvent Exchange," Journal of Controlled Release 100 (2004) pp. 379-388. 2004.
"Final Office Action," for U.S. Appl. No. 16/696,234 dated Dec. 10, 2021 (10 pages).
"International Preliminary Report on Patentability," for PCT Application No. PCT/US2019/063311 dated Jun. 10, 2021 (9 pages).
"Non-Final Office Action," for U.S. Appl. No. 16/696,234 dated Jun. 3, 2021 (53 pages).
"Non-Final Office Action," for U.S. Appl. No. 16/696,234 dated Mar. 21, 2022 (9 pages).
"Response to Final Office Action," for U.S. Appl. No. 16/696,234 filed with the USPTO dated Mar. 8, 2022 (11 pages).
"Response to Non-Final Office Action," for U.S. Appl. No. 16/696,234 filed with the USPTO dated Aug. 25, 2021 (10 pages).
"Notice of Allowance,"for U.S. Appl. No. 16/696,234 dated Dec. 14, 2022 (13 pages).
"Pre-Appeal Examination Report," for Japanese Patent Application No. 2015-539837 dated Mar. 8, 2019 (5 pages), with English Translation.
"Response to Non-Final Office Action," for U.S. Appl. No. 16/696,234 filed Jul. 19, 2022 (13 pages).

\* cited by examiner

APPARATUS AND METHODS FOR COATING MEDICAL DEVICES

This application claims the benefit of U.S. Provisional Application No. 62/846,920, filed May 13, 2019, the content of which is herein incorporated by reference in its entirety.

FIELD

Embodiments herein relate to coating apparatus and methods for coating medical devices. More specifically, embodiments herein relate to coating apparatus with two-part fluid applicators and related methods for coating medical devices.

BACKGROUND

Functional improvements to implantable or insertable medical devices can be achieved by coating the surface of the device. For example, a coating formed on the surface of the device can provide improved lubricity, improved biocompatibility, or drug delivery properties to the surface. In turn, this can improve movement of the device in the body, extend the functional life of the device, or treat a medical condition near the site of implantation. However, various challenges exist for the design and use of coating apparatus designed to provide coatings to medical devices.

Traditional coating methods, such as dip coating, are often undesirable as they may result in flawed coatings that could compromise the function of the device or present problems during use. These methods can also result in coating inaccuracies, which can be manifested in variable amounts of the coated material being deposited on the surface of the device. When a drug is included in the coating material, it is often necessary to deliver precise amounts of the agent to the surface of the device to ensure that a subject receiving the coated device receives a proper dose of the agent. However, it has been difficult to achieve a great degree of consistency using traditional coating methods and machines.

SUMMARY

Aspects herein relate to coating apparatus and methods for coating medical devices. In an embodiment, a coating system is included having a two-part fluid applicator defining a central channel, the two-part fluid applicator can include a first part having a first degree of flexibility; and a second part having a second degree of flexibility. The system can further include a fluid supply conduit in fluid communication with the fluid applicator; and a fluid supply reservoir in fluid communication with the fluid supply conduit.

In an embodiment, a method of coating a rotatable medical device is included, the method including mounting the rotatable medical device on a rotation mechanism; positioning a two-part fluid applicator to be in contact with the rotatable device; the two-part fluid applicator defining a central channel and can include a first part having a first degree of flexibility; and a second part having a second degree of flexibility. The method can further include rotating the rotatable medical device with the rotation mechanism; and conveying a coating composition from a fluid supply reservoir, through a fluid supply conduit, and through the two-part fluid applicator and onto a surface of the rotatable medical device.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Coatings are frequently applied onto the surfaces of various medical devices including, but not limited to, catheters and particularly balloon catheters. It is typically desirable for such coatings to be as uniform (in terms of thickness, composition, etc.) as possible.

In has been discovered that for direct-contact coating processes (e.g., where an applicator makes physical contact with the device to be coated) the uniformity and nature of the coating is greatly influenced by the structure of the applicator.

Embodiments herein can be used to apply uniform coatings, such as coatings including active agents, onto various medical devices, such as onto the balloons of drug coated or drug eluting balloon catheters, that have substantially uniform active agent concentrations along the length of the medical device. While not intending to be bound by theory, it is believed two-part coating applicators used with embodiments herein can enable better and more uniform contact between the tip of the applicator and the surface of the device to be coated, which leads to more uniform coatings. In some embodiments, the distal portion (the portion making direct contact with the surface to be coated) of the two-part coating applicator can have a larger diameter than the proximal portion of the two-part coating applicator. While not intending to be bound by theory, it is believed that this larger diameter can result in a larger pool of coating material near the contact point between the coating applicator and the device to be coated and this can also promote more uniform coatings.

Figure 1:
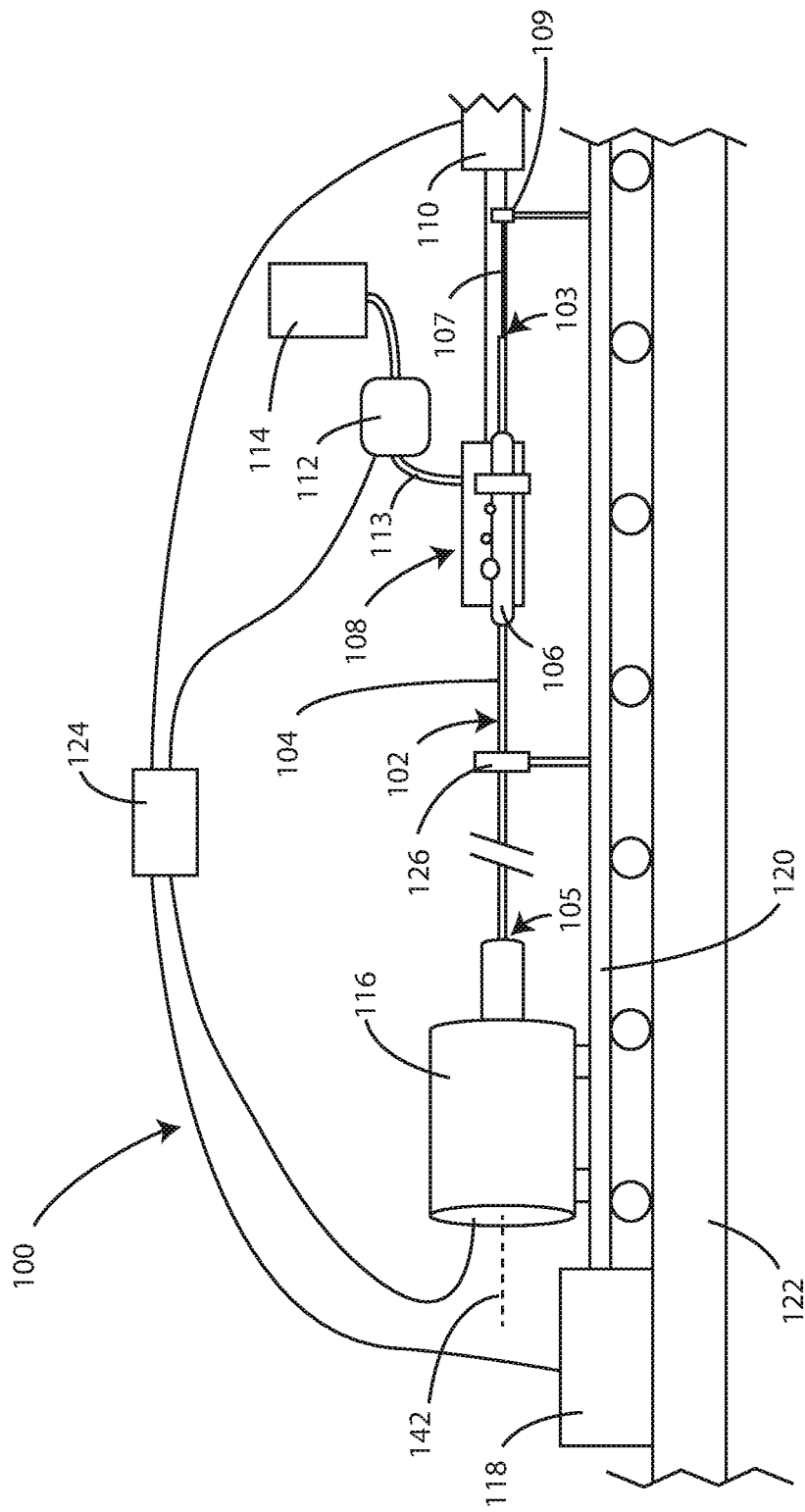
FIG. 1 is a schematic side view of a coating apparatus in accordance with various embodiments herein.

Referring now to FIG. 1, a schematic side view is shown of a coating apparatus 100 in accordance with various embodiments herein. The orientation of elements of the coating apparatus 100 in this view are just provided by way of example and it will be appreciated that the orientation of individual components can be configured differently, such as reversed, as well as the orientation of the whole apparatus. The coating apparatus 100 is shown in conjunction with a medical device 102 (which could be a drug coated balloon catheter, or another cylindrical or rollable device). In this example, the medical device 102 can include a catheter shaft 104 and a balloon 106. The balloon 106 can assume a deflated configuration and an inflated configuration. The medical device 102 can include a distal end 103 and a proximal end 105. The medical device 102 can include a proximal end manifold (not shown).

The coating apparatus 100 can include a coating application unit 108. The coating application unit 108 can include various components including, but not limited to a two-part applicator. The coating apparatus 100 can further include, in some embodiments, an axial motion mechanism 110 (axial with respect to the axis of rotation of the balloon catheter and thus parallel to the lengthwise axis of the balloon catheter) that can function to move one or more components of the coating application unit 108. The axial motion mechanism 110 can include an electric motor and, in some cases, gears, belts and/or chains. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. However, it will be appreciated that in other embodiments, the coating application unit 108 can remain stationary.

Coating of the balloon 106 to make it drug coated can occur starting at the proximal end of the balloon and proceeding to the distal end. However, in other embodiments, coating of the balloon 106 can occur starting at the distal end of the balloon and proceeding to the proximal end. In some embodiments, coating can take place with a single pass of the coating application unit 108 with respect to the balloon. However, in other embodiments, multiple passes of the coating application unit with respect to the balloon can be made.

The coating apparatus 100 can further include a fluid pump 112. The fluid pump 112 can be, for example, a syringe pump. The fluid pump 112 can be in fluid communication with components of the coating application unit 108 (such as the fluid applicator) and with a fluid supply reservoir 114. The fluid pump 112 can operate to pump a coating composition at a rate sufficient to apply about 0.5 µl to about 10 µl of the coating composition per millimeter of length of the balloon or other device to be coated.

In some embodiments, the fluid pump 112 can operate to pump a coating composition at a rate sufficient to apply at least 0.05 µl, 0.1 µl, 0.3 µl, 0.5 µl, 0.8 µl, 1 µl, 1.25 µl, 1.5 µl, 1.75 µl, or 2.00 µl of the coating composition per millimeter of length of the balloon or other device to be coated. In some embodiments, the rate can be sufficient to apply less than or equal to 10 µl, 9 µl, 8 µl, 7 µl, 6 µl, 5 µl, 4 µl, 3 µl, or 2 µl of the coating composition per millimeter of length of the balloon or other device to be coated. In some embodiments, the rate can be sufficient to apply an amount falling within a range of 0.05 µl to 10 µl, or 0.1 µl to 9 µl, or 0.3 µl to 9 µl, or 0.5 µl to 8 µl, or 0.8 µl to 7 µl, or 1 µl to 6 µl, or 1.25 µl to 5 µl, or 1.5 µl to 4 µl, or 1.75 µl to 3 µl of the coating composition per millimeter of length of the balloon or other device to be coated.

The fluid pump 112 can cause the coating composition/fluid to move through a fluid supply conduit 113 and to the coating application unit 108.

The coating apparatus 100 can further include a rotation mechanism 116 (or rotating balloon catheter fixture). The rotation mechanism 116 can include an electric motor. In some embodiments, the rotation mechanism 116 can also include gears and/or belts, chains, etc.

The rotation mechanism 116 can be directly or indirectly coupled to the drug coated balloon catheter in order to rotate the medical device 102 around a rotation axis 142 (the lengthwise or major axis of the medical device 102). In some embodiments, the speed can be greater than or equal to 10 RPM, 30 RPM, 60 RPM, 90 RPM, 120 RPM, 150 RPM, 180 RPM, 210 RPM, 240 RPM, or 270 RPM. In some embodiments, the speed can be less than or equal to 1000 RPM, 900 RPM, 800 RPM, 700 RPM, 600 RPM, 500 RPM, 400 RPM, 300 RPM, 200 RPM, or 100 RPM. In some embodiments, the speed can fall within a range between any of the foregoing.

In some embodiments, a guide wire 107, passing through the central lumen of the catheter, can extend from the distal tip of the catheter and be inserted into a distal tip support ring 109 or guide. In this manner, the guide wire 107 can be used to support the distal tip of the balloon catheter to be coated while allowing the balloon catheter to rotate freely.

The coating apparatus 100 can further include, in some embodiments, an axial motion mechanism 118 which can be configured to move the medical device 102 in the direction of its lengthwise major axis. In some embodiments, axial motion can be substantially horizontal. In other embodiments, axial motion can be substantially vertical. In some embodiments, axial motion can be somewhere in between horizontal and vertical, depending on the orientation of the lengthwise axis of the balloon catheter. In some embodiments, the axial motion mechanism 118 can be a linear actuator. In some embodiments, the axial motion mechanism 118 can include an electric motor.

The coating apparatus 100 can further include a frame member 120 (in some embodiments this can also be referred to as an axial motion support rail). The frame member 120 can support other components of the coating apparatus 100 such as one or more guides 126. The frame member 120 can itself be support by a platform 122. The coating apparatus 100 can further include a controller 124 that can serve to control operation of the coating apparatus 100 including, specifically, fluid pump 112, axial motion mechanism 110, rotation mechanism 116, and axial motion mechanism 118. Further aspects of coating apparatus components are described in U.S. Pat. No. 10,099,041, the content of which is herein incorporated by reference.

Figure 2:
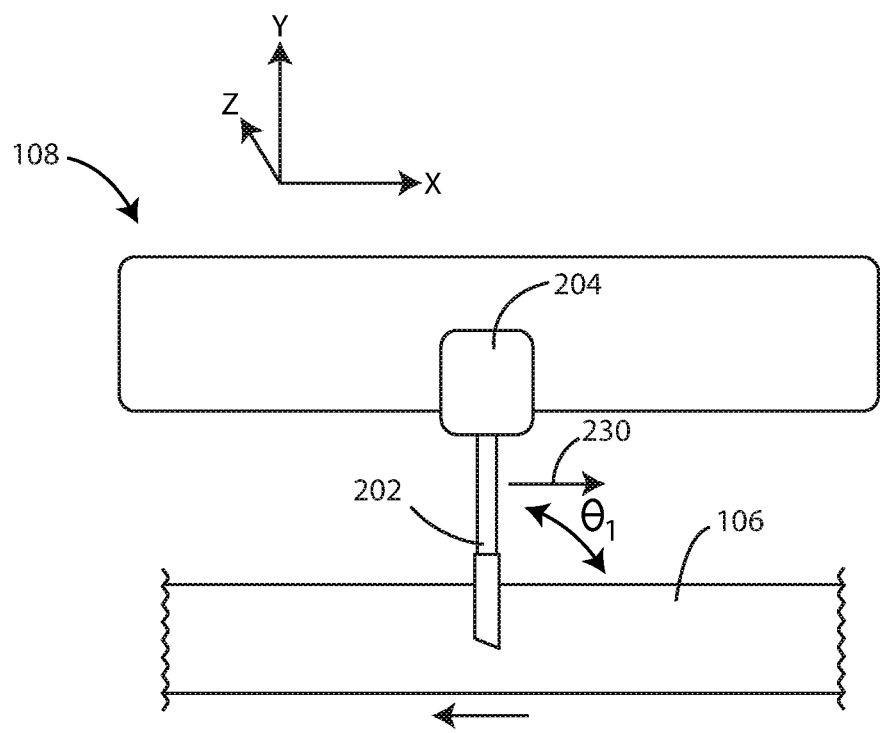
FIG. 2 is a schematic top view of a fluid applicator interfacing with a balloon catheter in accordance with various embodiments herein.

In various embodiments, the coating application unit can move, relative to the catheter or balloon. For example, referring now to FIG. 2, a schematic top view is shown of a fluid applicator 202 (which can be part of a coating application unit 108) interfacing with a balloon catheter (as merely one example of device that can be coated) in accordance with various embodiments herein. In this embodiment, it can be seen that the fluid applicator 202 moves in the direction of arrow 230 relative to the balloon 106 (or catheter shaft). It will be appreciated, however, that this movement is relative in the sense that in some embodiments the fluid applicator can move and the balloon can be stationary (or rotating, but stationary along its longitudinal axis), in some embodiments, the balloon can move (such as along its longitudinal axis) and the fluid applicator can be stationary, and in some embodiments both the balloon and the fluid applicator can move. In some cases, the fluid applicator 202 can move in a direction opposite to arrow 230. The speed of movement of the device to be coated relative to the coating application unit can vary depending on the amount of coating composition to be applied. In some embodiments the speed can be from about 0.02 centimeters per second to about 0.2 centimeters per second.

A fluid applicator actuator 204 can be included which can move the fluid applicator 202. In some embodiments, the fluid applicator actuator 204 can pivot the fluid applicator 202 such that the most proximal portion is relatively stationary, but the most distal portion moves up and down (e.g., the Z axis in FIG. 3). In some embodiments, the fluid applicator actuator 204 can move the entire fluid applicator 202 up and down. The fluid applicator actuator 204 can include an electric motor. In some embodiments, the fluid applicator actuator 204 can also include gears and/or belts, chains, etc.

In some embodiments, the fluid applicator actuator 204 can move the fluid applicator 202 with respect to a rotation axis defined by the rotation mechanism 116. In some embodiments, the fluid applicator actuator 204 can move the fluid applicator 202 toward the rotation axis 142 defined by the rotation mechanism 116 and into contact with a rotatable medical device supported by the rotation mechanism 116.

In some embodiments, the fluid applicator actuator 204 can further be configured to move the fluid applicator 202 toward a rotation axis defined by the rotation mechanism 116 and into contact with rotatable medical device supported by the rotation mechanism 116, and then move the fluid applicator 202 toward the rotation axis 142 an additional amount after making contact with the rotatable medical device. This additional movement can result in a degree of pressure (or static force) being applied onto the surface of the medical device and, in some cases, a degree of flexion of the fluid applicator 202. In an embodiment, the additional movement distance (such as additional movement along the Z axis after making contact with the device to be coated) can be from 50 to 1000 microns, or from 75 to 500 microns, or from 100 to 300 microns, or from 150 to 250 microns. However, in some embodiments, the fluid applicator 202 tip is just brought into contact with the device to be coated and no additional movement or pressure is applied (e.g., the tip just makes contact with the device to be coated).

It will be appreciated that based on the rotation of the drug coated balloon catheter and the movement of the balloon relative to the coating application unit that the path of the deposition of the coating onto the balloon follows a roughly helical path. It will be appreciated that the combination of the rotation speed of the drug coated balloon catheter and the speed of the movement of the balloon relative to the coating application unit can influence the amount of coating composition that is deposited at any given point and the nature of the helical path. For example, the coating material can be deposited in helical layers that partially overlap one another at their edges, helical layers wherein the edge of one turn substantially meets the edge of a previous turn, and helical layers wherein there are gaps in between subsequent helical turns. In some embodiments, these helical patterns can be configured to maximize release of the active agent. For example, in some embodiments, the apparatus can be used to coat device to produce helical ridges of the coating material on the balloon surface.

The fluid applicator 202 can be disposed at a particular angle ($\theta_1$) with respect to the balloon 106 (or catheter shaft 104 or other medical device component). In some embodiments, $\theta_1$ can be from about 30 degrees to about 150 degrees, or about 45 degrees to about 135 degrees, or from about 60 degrees to about 120 degrees, or from about 75 degrees to about 105 degrees, or from about 85 degrees to about 95 degrees, or in some embodiments about 90 degrees.

Figure 3:
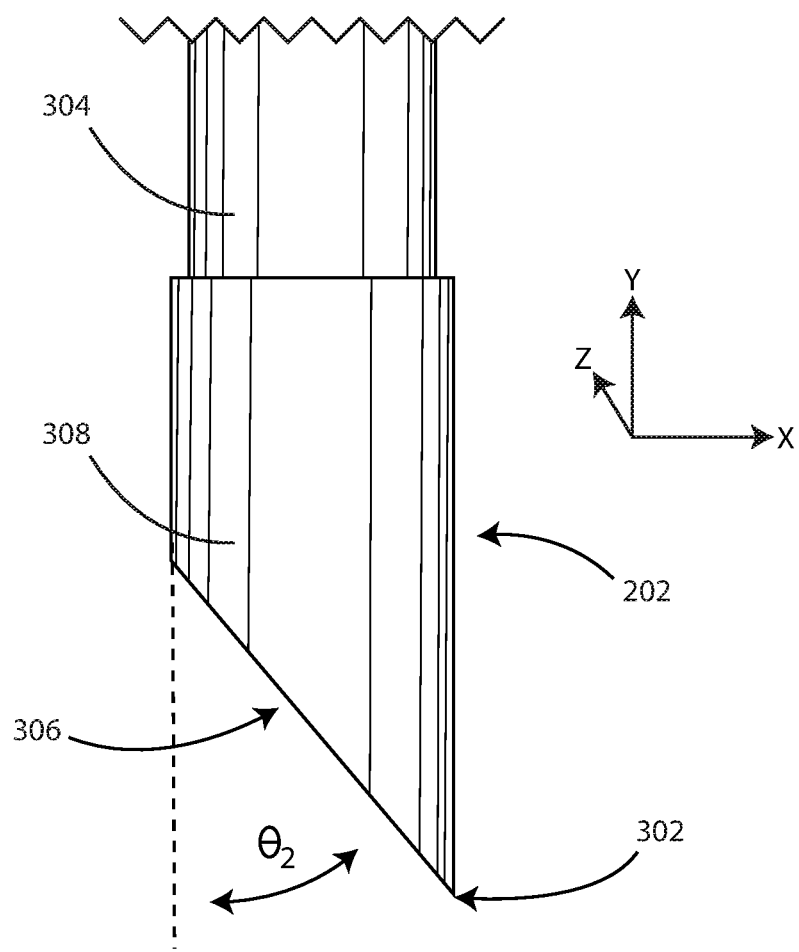
FIG. 3 is a schematic top view of a fluid applicator in accordance with various embodiments herein.

Referring now to FIG. 3, a schematic top view is shown of a fluid applicator 202 in accordance with various embodiments herein. The fluid applicator 202 can include a first part 304, a second part 308, and a tip area 302. The tip area 302 can have a face 306 that is angled with respect to the lengthwise axis of the fluid applicator 202. The face 306 can extend all the way across the width of the fluid applicator 202 in some embodiments. In some embodiments, the face 306 can have an angle $\theta_2$ with respect to a line parallel to the lengthwise axis of the fluid applicator 202. In some embodiments, angle $\theta_2$ can be from about 10 to about 80 degrees. In some embodiments, angle $\theta_2$ can be from about 15 to about 60 degrees, 25 to about 65 degrees, or from 30 to 75 degrees, or from 20 to 40 degrees. In some embodiments, angle $\theta_2$ can be from about 35 to about 55 degrees. In some embodiments, angle $\theta_2$ can be from about 40 to about 50 degrees. In some embodiments, angle $\theta_2$ can be about 30 degrees or about 45 degrees.

In some embodiments, the first part 304 of the fluid applicator can be made of a material that flexes. For example, the first part 304 can, in some embodiments, be sufficiently flexible such that it can move in the Z-axis direction by about 0.1 to about 4 mm, or from about 0.2 to 2 mm, or from about 0.3 to 1.5 mm. In some embodiments, the first part 304 can be about 0.5 to 5 centimeters, or from about 1 to 2 centimeters in length or can span an equal distance before connecting to another structure that is part of the coating apparatus. Movement in the Z-axis direction (through flexing or movement enabled by a separate structure connected to the shaft such as a pivoting mount) can be significant for purposes of maintaining continuity of contact between the fluid applicator and the surface of the device to be coated. In some embodiments, the fluid applicator 202 can be positioned such that it exerts a small degree of pressure against the surface of the medical device such that when an irregularity in the surface of the medical device is encountered the fluid applicator can move slightly in order to maintain contact with the balloon surface.

In some embodiments, the first part 304 of the fluid applicator can be formed of a translucent or transparent material. In other embodiments, the first part 304 can be substantially opaque.

Exemplary materials for the first part 304 of the fluid applicator can include, but are not limited to, polymers such as ethylene vinyl acetate (EVA), fluoropolymers (such as PTFE and PVDF), polyamides, polycarbonate, polystyrene, polyolefins (such as polyethylene and polypropylene), polyketones, polyurethane, polyvinylchloride, and the like. Other materials beyond polymers can also be used including, but not limited to, metals, glasses, composites, and the like. In some embodiments, the first part 304 is polypropylene.

In various embodiments, the first part 304 can be made from a tubing material of about 16 gauge to 22 gauge, or about 20 gauge, which corresponds to a wall thickness of about 0.035 inches (or 0.889 mm) and an inner diameter of about 0.58 mm. In cross-section, first part 304 can be circular, oval, polygonal, or the like.

In some embodiments, the second part 308 of the fluid applicator can be configured to flex, by way of physical configuration/size and/or by way of the material it is made from. In some embodiments, the second part 308 of the fluid applicator can be configured to be more flexible than the first part 304. For example, in some embodiments the second part 308 can have thinner walls than the first part 304. In some embodiments, the second part 308 can be made of a material that flexes to a greater degree than the material of the first part 304.

For example, the second part 308 can, in some embodiments, be sufficiently flexible such that it can move in the Z-axis direction by about 0.1 to about 1 cm, or from about 0.2 to 5 mm, or from about 0.3 to 1.5 mm. In some embodiments, the second part 308 can move in the Z-axis direction by at least 0.1, 0.2, 0.3, 0.4, 0.5, 0.6, 0.7, 0.8, 0.9, 1, 1.2, 1.5, 2, 2.5 or 3 mm more than the first part 304.

In some embodiments, the second part 308 can be made of a material having a softer durometer value than the first part 304. In some embodiments, the second part 308 can have a Shore A value of about 5 to 80, or about 20 to 80, or about 10 to 70, or about 10 to 50, or about 20 to 40. In various embodiments, the second part 308 can have a Shore A value that is less than (e.g., softer) than the first part 304.

In some embodiments, the second part 308 of the fluid applicator can be formed of a translucent or transparent material. In other embodiments, the second part 308 can be substantially opaque.

Exemplary materials for the second part 308 of the fluid applicator can include, but are not limited to, polymers such as ethylene vinyl acetate (EVA), fluoropolymers (such as PTFE and PVDF), polyamides, polycarbonate, polystyrene, polyolefins (such as polyethylene and polypropylene), polyketones, polyurethane, polyvinylchloride, and the like. Other materials beyond polymers can also be used including, but not limited to, metals, glasses, composites, and the like. In some embodiments, the second part 308 is a silicone (polysiloxane). In some embodiments, the second part 308 is an enhanced tear-resistant (ETR) silicone elastomer.

In various embodiments, the second part 308 can be made from a tubing material of about 16 gauge to 22 gauge, or about 20 gauge, which corresponds to a wall thickness of about 0.035 inches (or 0.889 mm). In some embodiments, the second part 308 can have an inner diameter of about 0.381 mm, 0.635 mm, 0.889 mm, or an amount falling within a range between any of the foregoing. In some embodiments, the second part 308 can have an outer diameter of about 1 mm, or 1.2 mm, or 1.4 mm, of an amount falling within a range between any of the foregoing.

In various embodiments, the second part 308 can have a size (gauge, outer diameter, inner diameter, etc.) that is larger than the first part 304. In cross-section, second part 308 can be circular, oval, polygonal, or the like. In some embodiments, the first part 304 includes a rotatable tube comprising an outer diameter and the first part 304 includes a rotatable tube comprising an outer diameter, and the outer diameter of the second part 308 is greater than the outer diameter of the first part 304. In some embodiments, the outer diameter of the first part 304 is from 1 mm to 5 mm and the outer diameter of the second part 308 is from greater than 1 mm to 7 mm. The inner diameter of the second part 308 can be sufficiently large for the second part 308 to fit over and overlap a segment of the first part 304.

The fluid applicator 202 (as the combination of the first part 304 and the second part 308) can be sufficiently flexible such that it can move in the Z-axis direction by about 0.1 to about 2 cm, or from about 0.2 to 1 cm, or from about 0.3 to 5 mm.

Figure 4:
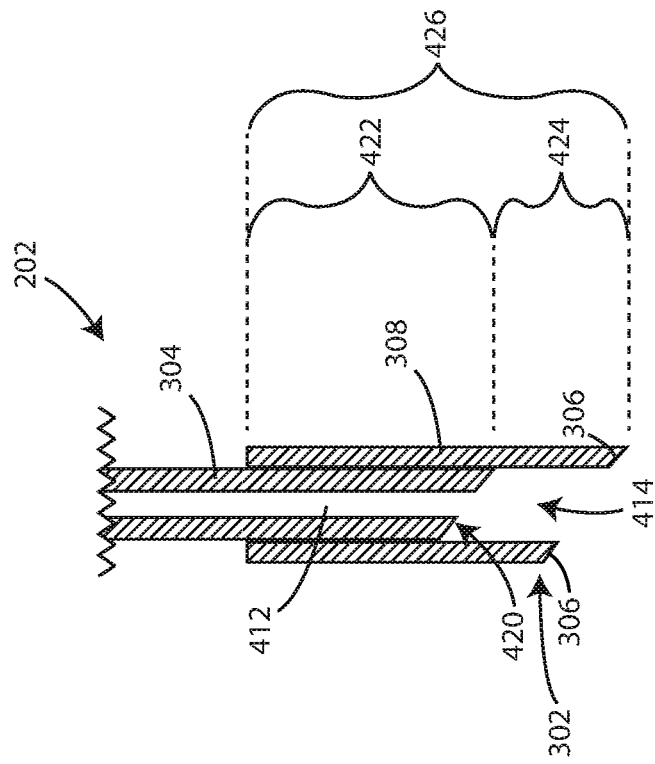
FIG. 4 is a schematic cross-sectional view of a fluid applicator in accordance with various embodiments herein.

Referring now to FIG. 4, a schematic cross-sectional view is shown of a fluid applicator 202 in accordance with various embodiments herein. The fluid applicator defines a central channel 412 through which a fluid coating composition can flow before exiting the tip through an orifice 414 (or aperture) which can be at least partly within the face 306. The diameter of the central channel 412 (or inner diameter of the first part 304) can be from about 1000 microns to about 100 microns, or from about 500 microns to about 200 microns. The distal end 420 of the first part 304 fits within the second part 308.

In various embodiments, the overall length 426 of the second part 308 can be from 1 mm to 50 mm, or from 2 mm to 30 mm, or from 10 mm to 30 mm. In various embodiments, the overlap 422 between the second part 308 and the first part 304 can be from 0.5 mm to 3 cm, or from 0.5 mm to 2 cm, or from 1 mm to 1 cm. In various embodiments, the overhang 424 (e.g., the distal end of the second part 308 extending beyond the distal end of the first part 304) of the second part 308 beyond the end of the first part 304 can be at least 0.5 mm, or from 0.5 mm to 2 cm, or from 0.5 mm to 1 cm, or from 1 mm to 2 mm. It will be appreciated, however, that in some embodiments the distal end of the first part 304 is substantially flush with the distal end of the second part 308 (see, e.g., FIG. 11).

Figure 5:
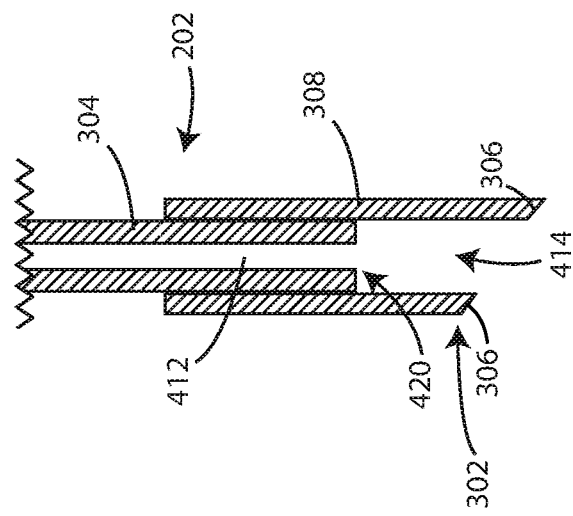
FIG. 5 is a schematic cross-sectional view of a fluid applicator in accordance with various embodiments herein.

The distal end 420 of the first part 304 can take on various shapes. In some embodiments, the distal end 420 of the first part 304 may be angled. In some embodiments, the distal end 420 of the first part 304 may be substantially flat. Referring now to FIG. 5, a schematic cross-sectional view is shown of a fluid applicator 202 in accordance with various embodiments herein. In this embodiment, the distal end 420 is substantially flat, versus angled as shown in FIG. 4.

Figure 6:
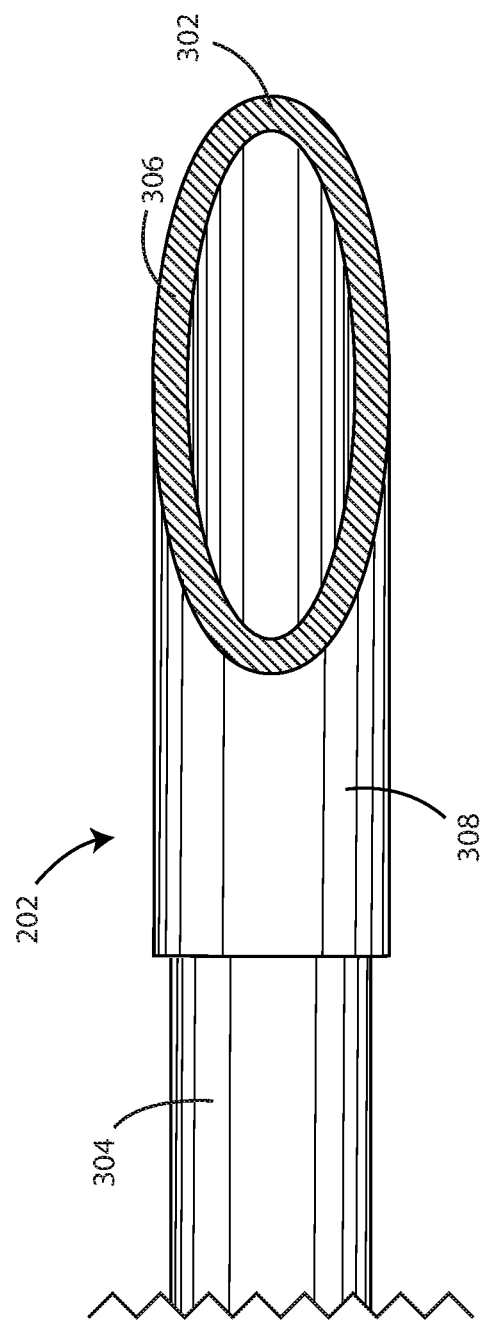
FIG. 6 is a schematic side view is shown of a portion of a fluid applicator in accordance with various embodiments herein.

Referring now to FIG. 6, a schematic side view is shown of a portion of a fluid applicator 202 in accordance with various embodiments herein. In this view, the first part 304 fits within the second part 308. The face 306 is disposed on the tip area 302 of the fluid applicator 202.

Figure 7:
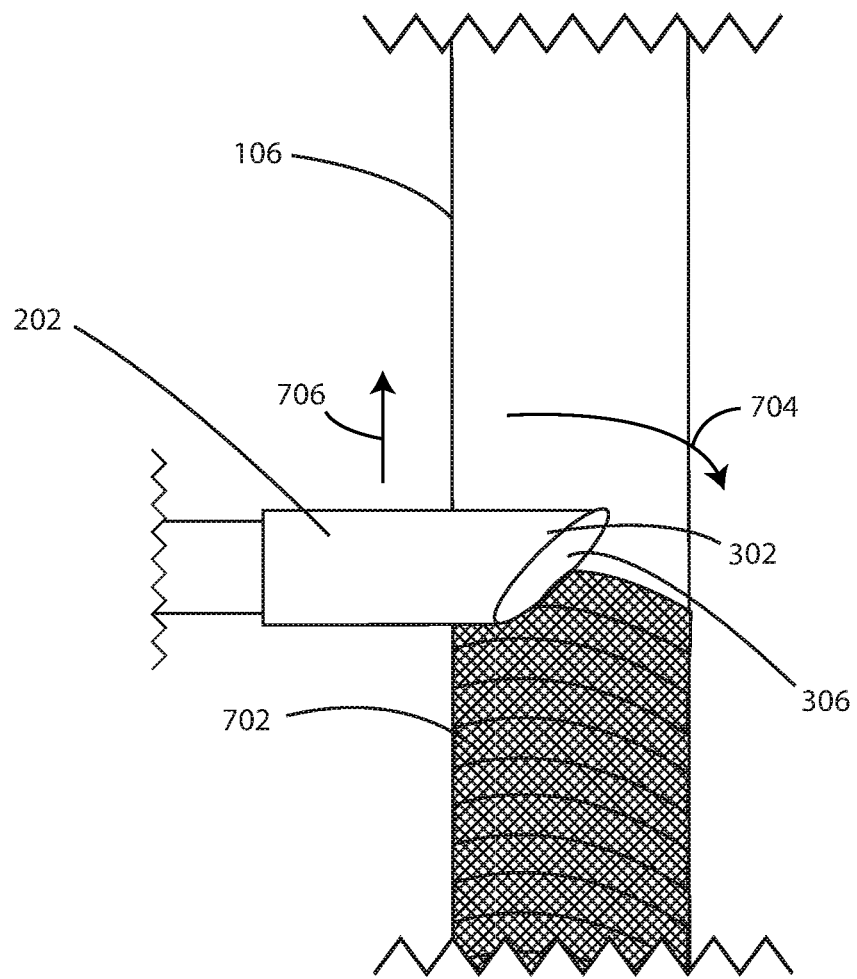
FIG. 7 is a schematic view of a fluid applicator in the process of depositing a coating onto a medical device in accordance with various embodiments herein.

The coating can be deposited in various ways using the fluid applicator. In some embodiments, the device-to-be-coated can rotate while the fluid application is in contact with a surface thereof and the coating composition can be pumped out of the fluid application. Referring now to FIG. 7, a schematic view is shown of a fluid applicator 202 in the process of depositing a coating 702 onto a balloon 106. The balloon 106 can rotate in the direction of arrow 704. The face 306 can be disposed on the tip area 302 of the fluid applicator 202. A coating material solution can come out of the face 306 and be deposited onto the surface of the balloon 106. The fluid applicator 202 can move in the direction of arrow 706 relative to the balloon 106.

Figure 8:
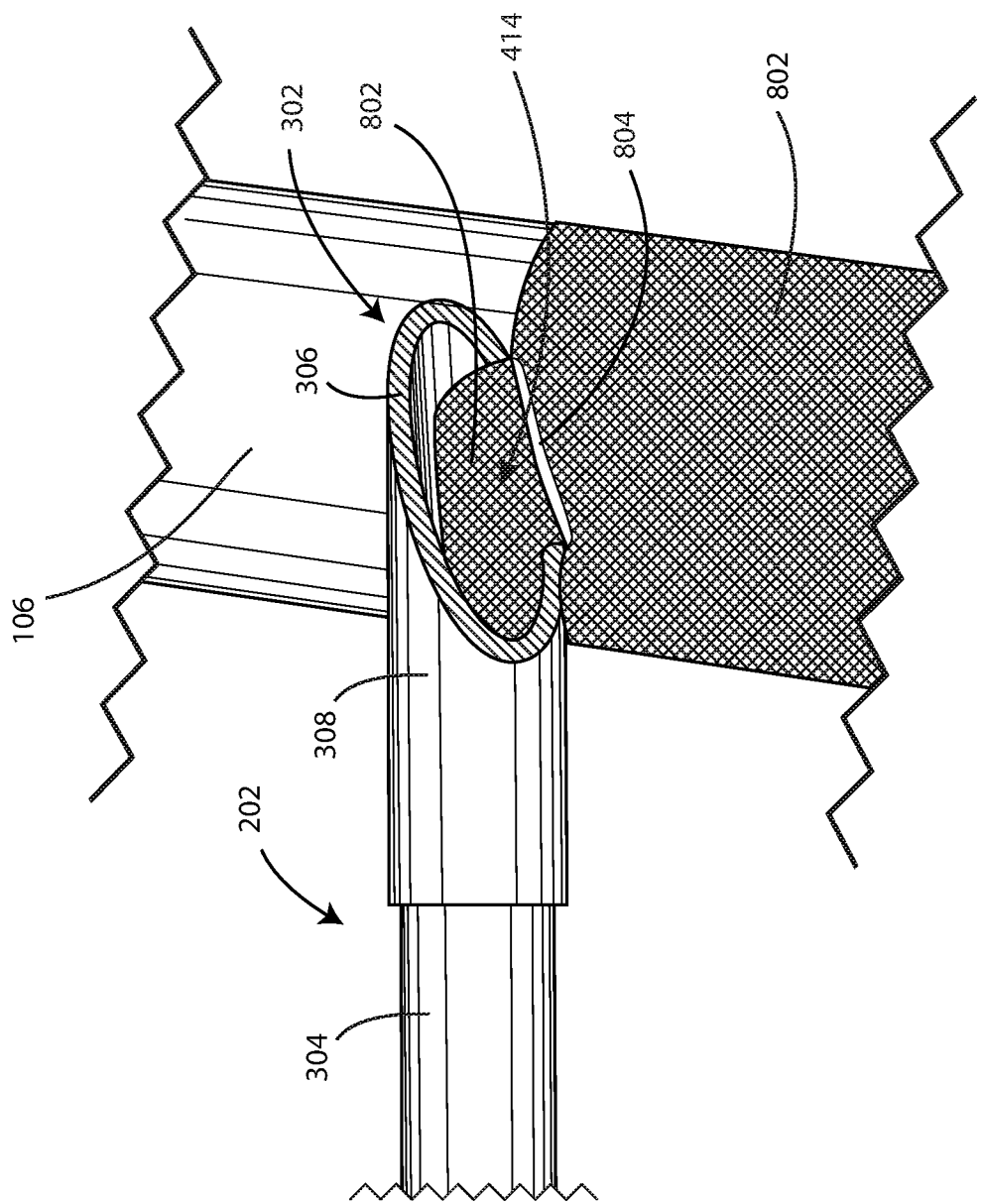
FIG. 8 is a schematic perspective view of a coating being applied to a medical device surface in accordance with various embodiments herein.

Referring now to FIG. 8, a schematic perspective view is shown of a fluid coating composition 802 being applied to a balloon 106 surface in accordance with various embodiments herein. The fluid coating composition 802 can pass out of an orifice 414 in the face 306. A pool (or capillary pool) of coating composition 804 can be present in the area near where the tip area 302 interfaces with the balloon 106. While not intending to be bound by theory, the pool of coating composition 804 is wider than if the fluid applicator only included first part 304 because the diameter of the second part 308 is greater than the diameter of the second part 308.

Figure 9:
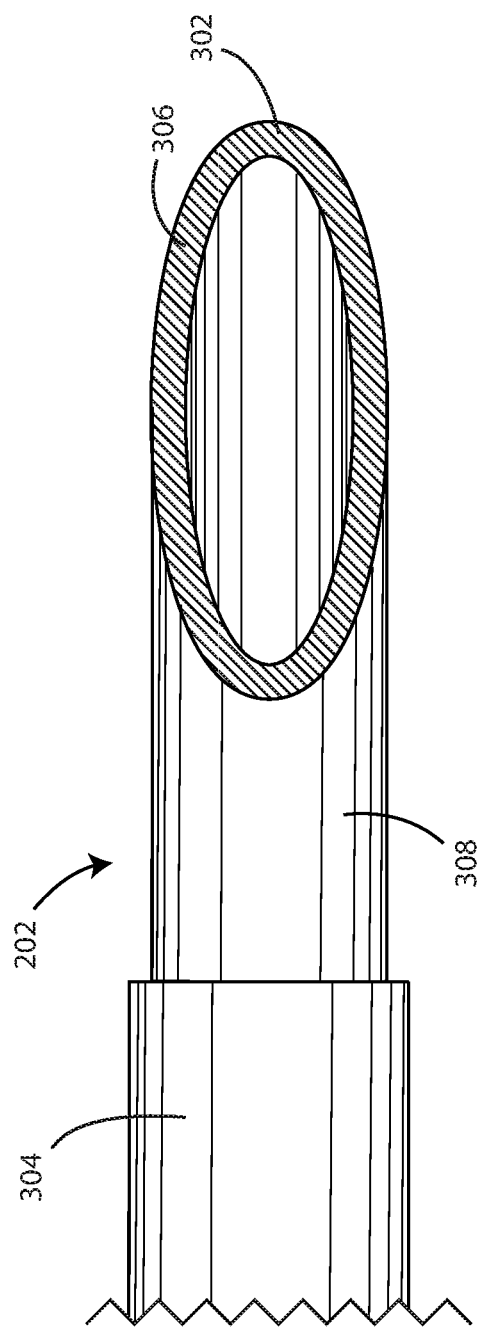
FIG. 9 is a schematic side view is shown of a portion of a fluid applicator in accordance with various embodiments herein.

Referring now to FIG. 9, a schematic side view is shown of a portion of a fluid applicator 202 in accordance with various embodiments herein. In this view, the second part 308 fits within the first part 304. The face 306 is disposed on the tip area 302 of the fluid applicator 202.

Figure 10:
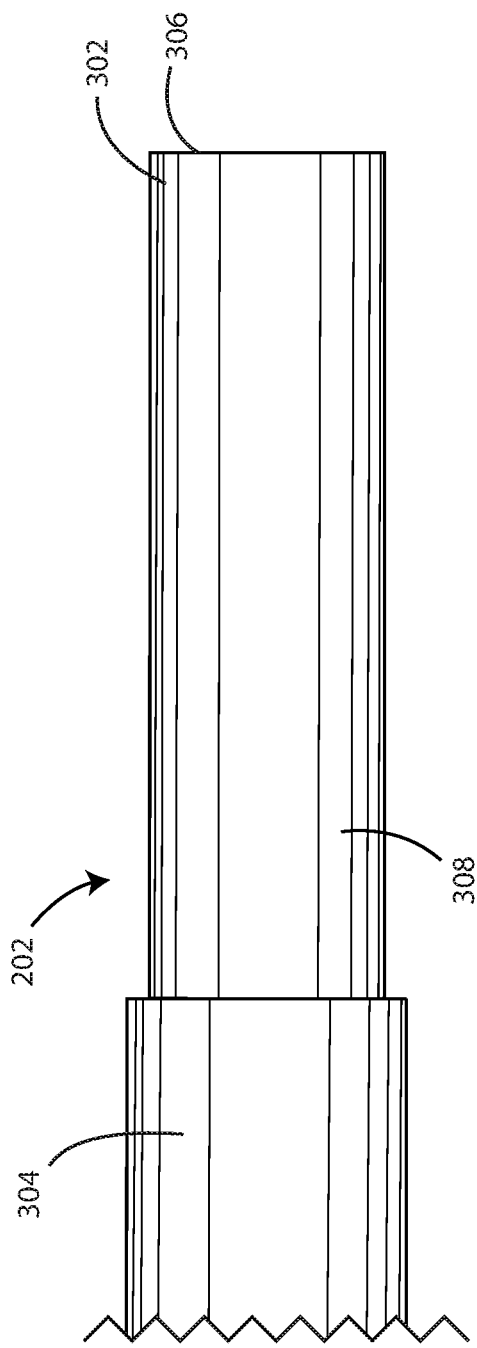
FIG. 10 is a schematic side view is shown of a portion of a fluid applicator in accordance with various embodiments herein.

In some embodiments, the tip area 302 can take on different configurations. In some embodiments, the tip area 302 may be substantially blunt, such that the face 306 lies in a plane that is substantially perpendicular to the lengthwise axis of the fluid applicator 202. Referring now to FIG. 10, a schematic side view is shown of a portion of a fluid applicator 202 in accordance with various embodiments herein. In this view, the face 306 is disposed on the tip area 302 of the fluid applicator 202 and is configured such that it lies in a plane that is substantially perpendicular to the lengthwise axis of the fluid applicator 202.

Figure 11:
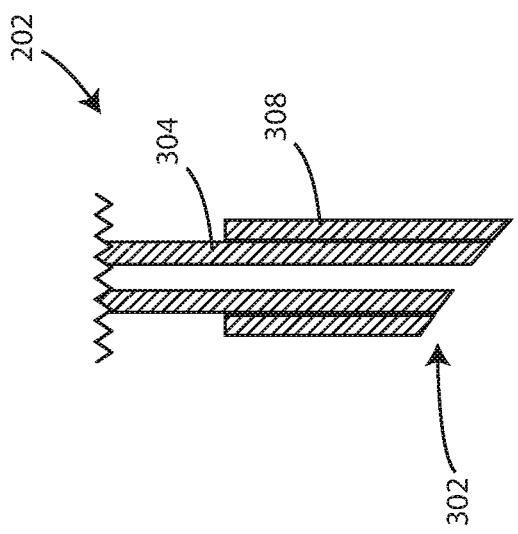
FIG. 11 is a schematic cross-sectional view of a fluid applicator in accordance with various embodiments herein.

Referring now to FIG. 11, a schematic side view is shown of a portion of a fluid applicator 202 in accordance with various embodiments herein. In this view, the first part 304 fits within the second part 308. In this view, the distal end of the first part 304 is substantially flush with the distal end of the second part 308, the distal ends forming the tip area 302 of the fluid applicator 202 in this embodiment.

Methods

Many different methods are contemplated herein, including, but not limited to, methods of making devices, methods of coating devices, and the like. In an embodiment, a method of coating a rotatable medical device is included, the method mounting the rotatable medical device on a rotation mechanism; positioning a two-part fluid applicator to be in contact with the rotatable device; the two-part fluid applicator defining a central channel and can include a first part having a first degree of flexibility; and a second part having a second degree of flexibility; rotating the rotatable medical device with the rotation mechanism; and conveying a coating composition from a fluid supply reservoir, through a fluid supply conduit, and through the two-part fluid applicator and onto a surface of the rotatable medical device.

In an embodiment of the method, positioning the two-part fluid applicator to be in contact with the rotatable device can include moving the fluid applicator toward a rotation axis defined by the rotation mechanism and into contact with rotatable medical device supported by the rotation mechanism.

In an embodiment of the method, positioning the two-part fluid applicator to be in contact with the rotatable device can include moving the fluid applicator toward a rotation axis defined by the rotation mechanism and into contact with rotatable medical device supported by the rotation mechanism. In some cases, the method can also include moving the fluid applicator toward the rotation axis an additional distance after making contact with the rotatable medical device (such as additional movement along the Z axis after making contact with the device to be coated). In an embodiment, the additional distance can include from 50 to 1000 microns, or from 75 to 500 microns, or from 100 to 300 microns, or from 150 to 250 microns.

Medical Devices

It will be appreciated that many different medical devices can be coated using equipment and methods herein. In various embodiments, rotatable medical device can be coated using equipment and methods described herein. In various embodiments, relatively long medical devices (such as those having a length that it is at least 20 times their diameter) can be coated using equipment and methods described herein.

One type of medical device is a balloon catheter. Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guide wire, and manifold. A balloon catheter generally includes an elongated catheter shaft with an inflatable balloon attached to a distal section of the catheter shaft. At a proximal end of the catheter shaft, there is typically a manifold. At the manifold end, placement of the catheter can be facilitated using a guide wire. Guide wires are small and maneuverable when inserted into an artery. Once the guide wire is moved to the target location, the catheter with balloon portion is then fed over the guide wire until the balloon reaches the target location in the vessel. The balloon is typically inserted into the arterial lumen of a patient and advanced through the lumen in an unexpanded state. The balloon is then inflated when the catheter reaches target site resulting in application of mechanical force sufficient to cause vessel dilation. The balloon is typically inflated using a fluid, which is injected through an inflation port. The manifold can control the fluid introduction within shaft for expansion of the balloon. The mechanics of fluid transfer and introduction within balloons vary according to the specific design of the catheter, and are well known in the art.

Figure 12:
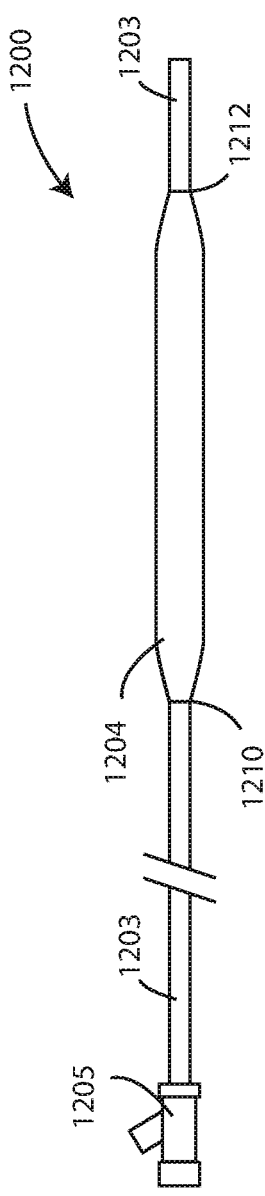
FIG. 12 is a schematic view of a medical device in accordance with various embodiments herein.

Referring now to FIG. 12, a schematic view of a medical device 1200 is shown. The medical device 1200 can optionally include a connection manifold 1205, a shaft 1203 having a surface, and an expandable portion 1204 (such as a balloon) having a surface. The expandable portion 1204 can include a proximal end 1210 and a distal end 1212. Coating segments can be disposed onto one or more of the shaft 1203 and the expandable portion 1204. In some embodiments, the expandable portion 1204 can include multiple coating segments thereon disposed adjacently to one another.

Coating Compositions

It will be appreciated that coating compositions applied onto medical devices herein as a fluid can include various components including, but not limited to, one or more active agents, carrier agents and/or solvents, polymers (including degradable or non-degradable polymers), cross-linking agents, excipients, and the like. The relative amounts of the components of the coating composition will depend on various factors including the desired amount of active agent to be applied to the balloon and the desired release rate of the active agent. Exemplary coating compositions are described in U.S. Publ. Pat. Appl. No. 2018/0110903, the content of which is herein incorporated by reference. Exemplary cross-linking agents are described in U.S. Pat. No. 8,889,760, the content of which is herein incorporated by reference.

In some embodiments, active agents can specifically include those wherein the coating composition is the form of a suspension or emulsion including active agent particles.

In some cases, the coating composition can be a true "solution" including one or more solvents and one or more dissolved solutes. However, in some cases the coating composition may include one or more components that are not dissolved. In some cases, the coating composition can be a suspension or mixture.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A coating system comprising:
a two-part fluid applicator defining a central fluid channel, the two-part fluid applicator comprising
a first part having a first degree of flexibility; and
a second part having a second degree of flexibility;
a fluid supply conduit in fluid communication with the two-part fluid applicator, the fluid supply conduit comprising a proximal end coupled to the fluid supply reservoir and a distal end coupled to the two-part fluid applicator; and
a fluid supply reservoir in fluid communication with the fluid supply conduit;
wherein the central fluid channel extends through the first part of the two-part fluid applicator and through the second part of the two-part fluid applicator, such that fluid flowing through the central fluid channel contacts the first part of the two-part fluid applicator and the second part of the two-part fluid applicator.

2. The coating system of claim 1, further comprising a rotation mechanism configured to mount and rotate a rotatable device to be coated.

3. The coating system of claim 2, further comprising a fluid applicator actuator to move the two-part fluid applicator with respect to a rotation axis defined by the rotation mechanism.

4. The coating system of claim 2, further comprising a fluid applicator actuator configured to move the two-part fluid applicator toward a rotation axis defined by the rotation mechanism and into contact with the rotatable device supported by the rotation mechanism.

5. The coating system of claim 4, wherein the fluid applicator actuator further moves the two-part fluid applicator toward the rotation axis an additional distance after making contact with the rotatable device resulting in a static force being applied to the rotatable medical device by the fluid applicator.

6. The coating system of claim 5, the additional distance comprising from 100 to 300 microns.

7. The coating system of claim 4, wherein the fluid applicator actuator stops moving the fluid applicator toward the rotation axis after making contact with the rotatable medical device resulting in substantially no static force being applied to the rotatable medical device by the fluid applicator.

8. The coating system of claim 3, the fluid applicator actuator comprising an electric motor.

9. The coating system of claim 1, wherein the second part overlaps the first part, such that a distal end of the first part is disposed within the second part.

10. The coating system of claim 1, wherein a distal end of the second part is flush with a distal end of the first part.

11. The coating system of claim 1, the first part comprising a rotatable tube comprising an outer diameter, the second part comprising a rotatable tube comprising an outer diameter, wherein the outer diameter of the second part is greater than the outer diameter of the first part.

12. The coating system of claim 11, the outer diameter of the first part from 1 mm to 5 mm and the outer diameter of the second part from greater than 1 mm to 7 mm.

13. The coating system of claim 1, the first part comprising a rotatable tube comprising an outer diameter, the second part comprising a rotatable tube comprising an inner diameter, wherein the inner diameter of the second part is sufficiently large for the second part to fit over and overlap a segment of the first part.

14. The coating system of claim 13, the first part comprising a distal end, the second part comprising a distal end, wherein the distal end of the second part extends at least 0.5 mm beyond the distal end of the first part.

15. The coating system of claim 1, the second part comprising a distal end, wherein the distal end of the second part defines a face disposed at an angle with respect to a lengthwise axis of the fluid applicator of about 30 to 75 degrees.

16. The coating system of claim 1, the second part comprising a distal end, wherein the distal end of the second part defines a face disposed at an angle with respect to a lengthwise axis of the two-part fluid applicator of about 40 to 50 degrees.

17. The coating system of claim 1, wherein a length of the two-part fluid applicator is 10 to 30 millimeters.

18. The coating system of claim 1, wherein the first part is less flexible than the second part.

19. The coating system of claim 1, wherein the first part is formed from a different material than the second part.

20. The coating system of claim 1, wherein the second part is formed from a polymer having a softer durometer value than the first part.

* * * * *